US008268321B2

(12) United States Patent
Kido et al.

(10) Patent No.: US 8,268,321 B2

(45) Date of Patent: Sep. 18, 2012

(54) ANTIGEN-DRUG VEHICLE ENABLING TRANSMUCOSAL AND TRANSDERMAL ADMINISTRATION, AND METHOD OF INDUCING MUCOSAL IMMUNITY AND MUCOSAL VACCINE AND DDS USING THE SAME

(75) Inventors: Hiroshi Kido, Tokushima (JP); Dai Mizuno, Tokushima (JP)

(73) Assignee: The University of Tokushima, Tokushima (JP)

(*) Notice: Subject to any disclaimer, the term of this patent is extended or adjusted under 35 U.S.C. 154(b) by 817 days.

(21) Appl. No.: 11/547,650

(22) PCT Filed: Mar. 22, 2005

(86) PCT No.: PCT/JP2005/005659

§ 371 (c)(1), (2), (4) Date: Nov. 21, 2006

(87) PCT Pub. No.: WO2005/097182

PCT Pub. Date: Oct. 20, 2005

(65) Prior Publication Data

US 2007/0141073 A1 Jun. 21, 2007

(30) Foreign Application Priority Data

Apr. 5, 2004 (JP) ................................. 2004-111249
Apr. 21, 2004 (JP) ................................. 2004-125036

(51) Int. Cl.

| | |
|---|---|
| ***A61K 39/00*** | (2006.01) |
| ***A61K 39/38*** | (2006.01) |
| ***A61K 39/12*** | (2006.01) |
| ***A61K 39/145*** | (2006.01) |

(52) U.S. Cl. ............... 424/184.1; 424/185.1; 424/204.1; 424/206.1

(58) Field of Classification Search ........................ None
See application file for complete search history.

(56) References Cited

FOREIGN PATENT DOCUMENTS

WO WO 96/30051 * 10/1996
WO WO 2003/035678 * 5/2003

OTHER PUBLICATIONS

Colman et al. 'Effects of amino acid sequence changes on antibody-antigen interactions.' Research in Immunology 145(1):33-36, 1994.*

Abaza et al. Effects of amino acid substitutions outside an antigenic site on protein binding to monoclonal antibodies of predetermined specificity obtained by peptide immunization: demonstration with region 94-100 (antigenic site 3) of myoglobin. J. Prot. Chem. 11(5):433-444, 1992.*

Lederrnan et al. 'A single amino acid substitution in a common African allele of the CD4 molecule ablates binding of the monoclonal antibody, OKT4.' Molec. Immunolo 28:1171-1181, 1991.*

Blumenthal et al. 'Definition of an Allergen.' Allergens and Allergen Immunotherapy. Ed. R Lockey, S. Bukantz and J. Bousquet. New York: Marcel Decker, 2004.37-50.*

Kinnunen et al. 'Potential/of/an altered peptide ligand of lipocalin allergen Bos d 2 for peptide immunotherapy.' J. Allergy Clin Immunol. 119(4):965-972, 2007.*

Kuby et al. 'Immunology.' Fourth Edition, Chapter 18: 449-465.*

Survanta product disclosure, Mar. 2009.*

Wang et al. 'Allergen-induced bronchial inflammation is associated with decreased levels of surfactanat proteins A and D in a murine model of asthma.' Clin. Exp. Allerg. 31:652-662, 2001.*

Pajno et al. 'Clinical and immunologic effects of long-term sublingual immunotherapy in asthmatic children sensitized to mites: a double-blind, placebo-controlled study.' Allergy. 55:842-849, 2000.*

Jobe et al. 'Surfactant effects on aerosolized and instilled adenoviral-mediated gene transfer.' Human Gene Therapy. 7(6):697-704, 1996.*

Prasad et al. 'Cutting edge: Recombinant adenoviruses induce CD8 T cell responses to an inserted protein whose expression is limited to nonimmune cells.' J. Immunol. 166:4809-4812, 2001.*

Tang et al. 'Recombinant adenovirus encoding the HA gene from swine H3N2 influenza virus partially protects mice from challenge with heterologous virus: A/HK/1/68 (H3N2).' Arch. Virol. 147:2125-2141, 2002.*

Wesley et al. 'Protection of Weaned Pigs by Vaccination with Human Adenovirus 5 Recombinant Viruses Expressing the Hemagglutinin and the Nucleoprotein of H3n2 Swine Influenza Virus.' Vaccine 22:3427-3434, 2004.*

Mizuno et al. 'Surfactant protein C is an essential constituent for mucosal adjuvanticity of Surfacten, acting as an antigen delivery vehicle and inducing both local and systemic immunity.' Vaccine 29:5368-5378, 2011.*

* cited by examiner

*Primary Examiner* — Nora Rooney

(74) *Attorney, Agent, or Firm* — Wenderoth, Lind & Ponack, L.L.P.

(57) ABSTRACT

Disclosed are an antigen-drug vehicle (AD vehicle) exerting a function of inducing the preferential and selective production of an antigen-specific secretory IgA antibody, local immunity or mucosal immunity; a method of inducing mucosal immunity, a mucosal vaccine and a preventive or a remedy for allergy using the above AD vehicle; and a transmucosal or transdermal DDS using the above vehicle.

5 Claims, 9 Drawing Sheets c)

d)

a)

b)

a)

b)

a)

b)

a)

b)

(a)

(b)

(c)

SEQUENCE LISTING

```
<160> NUMBER OF SEQ ID NOS: 21

<210> SEQ ID NO 1
<211> LENGTH: 1146
<212> TYPE: DNA
<213> ORGANISM: Homo sapiens
<220> FEATURE:
<221> NAME/KEY: CDS
<222> LOCATION: (1)..(1143)
<223> OTHER INFORMATION:

<400> SEQUENCE: 1

atg gct gag tca cac ctg ctg cag tgg ctg ctg ctg ctg ccc acg       48
Met Ala Glu Ser His Leu Leu Gln Trp Leu Leu Leu Leu Pro Thr
1               5                   10                  15

ctc tgt ggc cca ggc act gct gcc tgg acc acc tca tcc ttg gcc tgt       96
Leu Cys Gly Pro Gly Thr Ala Ala Trp Thr Thr Ser Ser Leu Ala Cys
            20                  25                  30

gcc cag ggc cct gag ttc tgg tgc caa agc ctg gag caa gca ttg cag      144
Ala Gln Gly Pro Glu Phe Trp Cys Gln Ser Leu Glu Gln Ala Leu Gln
        35                  40                  45

tgc aga gcc cta ggg cat tgc cta cag gaa gtc tgg gga cat gtg gga      192
Cys Arg Ala Leu Gly His Cys Leu Gln Glu Val Trp Gly His Val Gly
    50                  55                  60

gcc gat gac cta tgc caa gag tgt gag gac atc gtc cac atc ctt aac      240
Ala Asp Asp Leu Cys Gln Glu Cys Glu Asp Ile Val His Ile Leu Asn
65                  70                  75                  80

aag atg gcc aag gag gcc att ttc cag gac acg atg agg aag ttc ctg      288
Lys Met Ala Lys Glu Ala Ile Phe Gln Asp Thr Met Arg Lys Phe Leu
                85                  90                  95

gag cag gag tgc aac gtc ctc ccc ttg aag ctg ctc atg ccc cag tgc      336
Glu Gln Glu Cys Asn Val Leu Pro Leu Lys Leu Leu Met Pro Gln Cys
            100                 105                 110

aac caa gtg ctt gac gac tac ttc ccc ctg gtc atc gac tac ttc cag      384
Asn Gln Val Leu Asp Asp Tyr Phe Pro Leu Val Ile Asp Tyr Phe Gln
        115                 120                 125

aac cag act gac tca aac ggc atc tgt atg cac ctg ggc ctg tgc aaa      432
Asn Gln Thr Asp Ser Asn Gly Ile Cys Met His Leu Gly Leu Cys Lys
    130                 135                 140

tcc cgg cag cca gag cca gag cag gag cca ggg atg tca gac ccc ctg      480
Ser Arg Gln Pro Glu Pro Glu Gln Glu Pro Gly Met Ser Asp Pro Leu
145                 150                 155                 160

ccc aaa cct ctg cgg gac cct ctg cca gac cct ctg ctg gac aag ctc      528
Pro Lys Pro Leu Arg Asp Pro Leu Pro Asp Pro Leu Leu Asp Lys Leu
                165                 170                 175

gtc ctc cct gtg ctg ccc ggg gcc ctc cag gcg agg cct ggg cct cac      576
Val Leu Pro Val Leu Pro Gly Ala Leu Gln Ala Arg Pro Gly Pro His
            180                 185                 190

aca cag gat ctc tcc gag cag caa ttc ccc att cct ctc ccc tat tgc      624
Thr Gln Asp Leu Ser Glu Gln Gln Phe Pro Ile Pro Leu Pro Tyr Cys
        195                 200                 205

tgg ctc tgc agg gct ctg atc aag cgg atc caa gcc atg att ccc aag      672
Trp Leu Cys Arg Ala Leu Ile Lys Arg Ile Gln Ala Met Ile Pro Lys
```

-continued

```
    210                 215                 220

ggt gcg cta gct gtg gca gtg gcc cag gtg tgc cgc gtg gta cct ctg      720
Gly Ala Leu Ala Val Ala Val Ala Gln Val Cys Arg Val Val Pro Leu
225                 230                 235                 240

gtg gcg ggc ggc atc tgc cag tgc ctg gct gag cgc tac tcc gtc atc      768
Val Ala Gly Gly Ile Cys Gln Cys Leu Ala Glu Arg Tyr Ser Val Ile
                245                 250                 255

ctg ctc gac acg ctg ctg ggc cgc atg ctg ccc cag ctg gtc tgc cgc      816
Leu Leu Asp Thr Leu Leu Gly Arg Met Leu Pro Gln Leu Val Cys Arg
            260                 265                 270

ctc gtc ctc cgg tgc tcc atg gat gac agc gct ggc cca agg tcg ccg      864
Leu Val Leu Arg Cys Ser Met Asp Asp Ser Ala Gly Pro Arg Ser Pro
        275                 280                 285

aca gga gaa tgg ctg ccg cga gac tct gag tgc cac ctc tgc atg tcc      912
Thr Gly Glu Trp Leu Pro Arg Asp Ser Glu Cys His Leu Cys Met Ser
    290                 295                 300

gtg acc acc cag gcc ggg aac agc agc gag cag gcc ata cca cag gca      960
Val Thr Thr Gln Ala Gly Asn Ser Ser Glu Gln Ala Ile Pro Gln Ala
305                 310                 315                 320

atg ctc cag gcc tgt gtt ggc tcc tgg ctg gac agg gaa aag tgc aag     1008
Met Leu Gln Ala Cys Val Gly Ser Trp Leu Asp Arg Glu Lys Cys Lys
                325                 330                 335

caa ttt gtg gag cag cac acg ccc cag ctg ctg acc ctg gtg ccc agg     1056
Gln Phe Val Glu Gln His Thr Pro Gln Leu Leu Thr Leu Val Pro Arg
            340                 345                 350

ggc tgg gat gcc cac acc acc tgc cag gcc ctc ggg gtg tgt ggg acc     1104
Gly Trp Asp Ala His Thr Thr Cys Gln Ala Leu Gly Val Cys Gly Thr
        355                 360                 365

atg tcc agc cct ctc cag tgt atc cac agc ccc gac ctt tga             1146
Met Ser Ser Pro Leu Gln Cys Ile His Ser Pro Asp Leu
    370                 375                 380


<210> SEQ ID NO 2
<211> LENGTH: 381
<212> TYPE: PRT
<213> ORGANISM: Homo sapiens

<400> SEQUENCE: 2

Met Ala Glu Ser His Leu Leu Gln Trp Leu Leu Leu Leu Leu Pro Thr
1               5                   10                  15

Leu Cys Gly Pro Gly Thr Ala Ala Trp Thr Thr Ser Ser Leu Ala Cys
            20                  25                  30

Ala Gln Gly Pro Glu Phe Trp Cys Gln Ser Leu Glu Gln Ala Leu Gln
        35                  40                  45

Cys Arg Ala Leu Gly His Cys Leu Gln Glu Val Trp Gly His Val Gly
    50                  55                  60

Ala Asp Asp Leu Cys Gln Glu Cys Glu Asp Ile Val His Ile Leu Asn
65                  70                  75                  80

Lys Met Ala Lys Glu Ala Ile Phe Gln Asp Thr Met Arg Lys Phe Leu
                85                  90                  95

Glu Gln Glu Cys Asn Val Leu Pro Leu Lys Leu Leu Met Pro Gln Cys
            100                 105                 110

Asn Gln Val Leu Asp Asp Tyr Phe Pro Leu Val Ile Asp Tyr Phe Gln
        115                 120                 125

Asn Gln Thr Asp Ser Asn Gly Ile Cys Met His Leu Gly Leu Cys Lys
    130                 135                 140

Ser Arg Gln Pro Glu Pro Glu Gln Glu Pro Gly Met Ser Asp Pro Leu
145                 150                 155                 160
```

-continued

```
Pro Lys Pro Leu Arg Asp Pro Leu Pro Asp Pro Leu Leu Asp Lys Leu
                165                 170                 175

Val Leu Pro Val Leu Pro Gly Ala Leu Gln Ala Arg Pro Gly Pro His
            180                 185                 190

Thr Gln Asp Leu Ser Glu Gln Gln Phe Pro Ile Pro Leu Pro Tyr Cys
        195                 200                 205

Trp Leu Cys Arg Ala Leu Ile Lys Arg Ile Gln Ala Met Ile Pro Lys
    210                 215                 220

Gly Ala Leu Ala Val Ala Val Ala Gln Val Cys Arg Val Val Pro Leu
225                 230                 235                 240

Val Ala Gly Gly Ile Cys Gln Cys Leu Ala Glu Arg Tyr Ser Val Ile
                245                 250                 255

Leu Leu Asp Thr Leu Leu Gly Arg Met Leu Pro Gln Leu Val Cys Arg
            260                 265                 270

Leu Val Leu Arg Cys Ser Met Asp Asp Ser Ala Gly Pro Arg Ser Pro
        275                 280                 285

Thr Gly Glu Trp Leu Pro Arg Asp Ser Glu Cys His Leu Cys Met Ser
    290                 295                 300

Val Thr Thr Gln Ala Gly Asn Ser Ser Glu Gln Ala Ile Pro Gln Ala
305                 310                 315                 320

Met Leu Gln Ala Cys Val Gly Ser Trp Leu Asp Arg Glu Lys Cys Lys
                325                 330                 335

Gln Phe Val Glu Gln His Thr Pro Gln Leu Leu Thr Leu Val Pro Arg
            340                 345                 350

Gly Trp Asp Ala His Thr Thr Cys Gln Ala Leu Gly Val Cys Gly Thr
        355                 360                 365

Met Ser Ser Pro Leu Gln Cys Ile His Ser Pro Asp Leu
    370                 375                 380


<210> SEQ ID NO 3
<211> LENGTH: 594
<212> TYPE: DNA
<213> ORGANISM: Homo sapiens
<220> FEATURE:
<221> NAME/KEY: CDS
<222> LOCATION: (1)..(591)
<223> OTHER INFORMATION:

<400> SEQUENCE: 3

atg gat gtg ggc agc aaa gag gtc ctg atg gag agc ccg ccg gac tac       48
Met Asp Val Gly Ser Lys Glu Val Leu Met Glu Ser Pro Pro Asp Tyr
1               5                   10                  15

tcc gca gct ccc cgg ggc cga ttt ggc att ccc tgc tgc cca gtg cac       96
Ser Ala Ala Pro Arg Gly Arg Phe Gly Ile Pro Cys Cys Pro Val His
            20                  25                  30

ctg aaa cgc ctt ctt atc gtg gtg gtg gtg gtg gtc ctc atc gtc gtg      144
Leu Lys Arg Leu Leu Ile Val Val Val Val Val Val Leu Ile Val Val
        35                  40                  45

gtg att gtg gga gcc ctg ctc atg ggt ctc cac atg agc cag aaa cac      192
Val Ile Val Gly Ala Leu Leu Met Gly Leu His Met Ser Gln Lys His
    50                  55                  60

acg gag atg gtt ctg gag atg agc att ggg gcg ccg gaa gcc cag caa      240
Thr Glu Met Val Leu Glu Met Ser Ile Gly Ala Pro Glu Ala Gln Gln
65                  70                  75                  80

cgc ctg gcc ctg agt gag cac ctg gtt acc act gcc acc ttc tcc atc      288
Arg Leu Ala Leu Ser Glu His Leu Val Thr Thr Ala Thr Phe Ser Ile
                85                  90                  95

ggc tcc act ggc ctc gtg gtg tat gac tac cag cag ctg ctg atc gcc      336
Gly Ser Thr Gly Leu Val Val Tyr Asp Tyr Gln Gln Leu Leu Ile Ala
```

```
            100                 105                 110

tac aag cca gcc cct ggc acc tgc tgc tac atc atg aag ata gct cca      384
Tyr Lys Pro Ala Pro Gly Thr Cys Cys Tyr Ile Met Lys Ile Ala Pro
        115                 120                 125

gag agc atc ccc agt ctt gag gct ctc act aga aaa gtc cac aac ttc      432
Glu Ser Ile Pro Ser Leu Glu Ala Leu Thr Arg Lys Val His Asn Phe
    130                 135                 140

cag atg gaa tgc tct ctg cag gcc aag ccc gca gtg cct acg tct aag      480
Gln Met Glu Cys Ser Leu Gln Ala Lys Pro Ala Val Pro Thr Ser Lys
145                 150                 155                 160

ctg ggc cag gca gag ggg cga gat gca ggc tca gca ccc tcc gga ggg      528
Leu Gly Gln Ala Glu Gly Arg Asp Ala Gly Ser Ala Pro Ser Gly Gly
                165                 170                 175

gac ccg gcc ttc ctg ggc atg gcc gtg aac acc ctg tgt ggc gag gtg      576
Asp Pro Ala Phe Leu Gly Met Ala Val Asn Thr Leu Cys Gly Glu Val
            180                 185                 190

ccg ctc tac tac atc tag                                              594
Pro Leu Tyr Tyr Ile
        195


<210> SEQ ID NO 4
<211> LENGTH: 197
<212> TYPE: PRT
<213> ORGANISM: Homo sapiens

<400> SEQUENCE: 4

Met Asp Val Gly Ser Lys Glu Val Leu Met Glu Ser Pro Pro Asp Tyr
1               5                   10                  15

Ser Ala Ala Pro Arg Gly Arg Phe Gly Ile Pro Cys Cys Pro Val His
            20                  25                  30

Leu Lys Arg Leu Leu Ile Val Val Val Val Val Val Leu Ile Val Val
        35                  40                  45

Val Ile Val Gly Ala Leu Leu Met Gly Leu His Met Ser Gln Lys His
    50                  55                  60

Thr Glu Met Val Leu Glu Met Ser Ile Gly Ala Pro Glu Ala Gln Gln
65                  70                  75                  80

Arg Leu Ala Leu Ser Glu His Leu Val Thr Thr Ala Thr Phe Ser Ile
                85                  90                  95

Gly Ser Thr Gly Leu Val Val Tyr Asp Tyr Gln Gln Leu Leu Ile Ala
            100                 105                 110

Tyr Lys Pro Ala Pro Gly Thr Cys Cys Tyr Ile Met Lys Ile Ala Pro
        115                 120                 125

Glu Ser Ile Pro Ser Leu Glu Ala Leu Thr Arg Lys Val His Asn Phe
    130                 135                 140

Gln Met Glu Cys Ser Leu Gln Ala Lys Pro Ala Val Pro Thr Ser Lys
145                 150                 155                 160

Leu Gly Gln Ala Glu Gly Arg Asp Ala Gly Ser Ala Pro Ser Gly Gly
                165                 170                 175

Asp Pro Ala Phe Leu Gly Met Ala Val Asn Thr Leu Cys Gly Glu Val
            180                 185                 190

Pro Leu Tyr Tyr Ile
        195


<210> SEQ ID NO 5
<211> LENGTH: 576
<212> TYPE: DNA
<213> ORGANISM: Homo sapiens
<220> FEATURE:
<221> NAME/KEY: CDS
```

<222> LOCATION: (1)..(573)
<223> OTHER INFORMATION:

<400> SEQUENCE: 5

```
atg gat gtg ggc agc aaa gag gtc ctg atg gag agc ccg ccg gac tac      48
Met Asp Val Gly Ser Lys Glu Val Leu Met Glu Ser Pro Pro Asp Tyr
1               5                   10                  15

tcc gca gct ccc cgg ggc cga ttt ggc att ccc tgc tgc cca gtg cac      96
Ser Ala Ala Pro Arg Gly Arg Phe Gly Ile Pro Cys Cys Pro Val His
            20                  25                  30

ctg aaa cgc ctt ctt atc gtg gtg gtg gtg gtg gtc ctc atc gtc gtg     144
Leu Lys Arg Leu Leu Ile Val Val Val Val Val Val Leu Ile Val Val
        35                  40                  45

gtg att gtg gga gcc ctg ctc atg ggt ctc cac atg agc cag aaa cac     192
Val Ile Val Gly Ala Leu Leu Met Gly Leu His Met Ser Gln Lys His
    50                  55                  60

acg gag atg gtt ctg gag atg agc att ggg gcg ccg gaa gcc cag caa     240
Thr Glu Met Val Leu Glu Met Ser Ile Gly Ala Pro Glu Ala Gln Gln
65                  70                  75                  80

cgc ctg gcc ctg agt gag cac ctg gtt acc act gcc acc ttc tcc atc     288
Arg Leu Ala Leu Ser Glu His Leu Val Thr Thr Ala Thr Phe Ser Ile
                85                  90                  95

ggc tcc act ggc ctc gtg gtg tat gac tac cag cag ctg ctg atc gcc     336
Gly Ser Thr Gly Leu Val Val Tyr Asp Tyr Gln Gln Leu Leu Ile Ala
            100                 105                 110

tac aag cca gcc cct ggc acc tgc tgc tac atc atg aag ata gct cca     384
Tyr Lys Pro Ala Pro Gly Thr Cys Cys Tyr Ile Met Lys Ile Ala Pro
        115                 120                 125

gag agc atc ccc agt ctt gag gct ctc act aga aaa gtc cac aac ttc     432
Glu Ser Ile Pro Ser Leu Glu Ala Leu Thr Arg Lys Val His Asn Phe
    130                 135                 140

cag gcc aag ccc gca gtg cct acg tct aag ctg ggc cag gca gag ggg     480
Gln Ala Lys Pro Ala Val Pro Thr Ser Lys Leu Gly Gln Ala Glu Gly
145                 150                 155                 160

cga gat gca ggc tca gca ccc tcc gga ggg gac ccg gcc ttc ctg ggc     528
Arg Asp Ala Gly Ser Ala Pro Ser Gly Gly Asp Pro Ala Phe Leu Gly
                165                 170                 175

atg gcc gtg aac acc ctg tgt ggc gag gtg ccg ctc tac tac atc tag     576
Met Ala Val Asn Thr Leu Cys Gly Glu Val Pro Leu Tyr Tyr Ile
            180                 185                 190
```

<210> SEQ ID NO 6
<211> LENGTH: 191
<212> TYPE: PRT
<213> ORGANISM: Homo sapiens

<400> SEQUENCE: 6

```
Met Asp Val Gly Ser Lys Glu Val Leu Met Glu Ser Pro Pro Asp Tyr
1               5                   10                  15

Ser Ala Ala Pro Arg Gly Arg Phe Gly Ile Pro Cys Cys Pro Val His
            20                  25                  30

Leu Lys Arg Leu Leu Ile Val Val Val Val Val Val Leu Ile Val Val
        35                  40                  45

Val Ile Val Gly Ala Leu Leu Met Gly Leu His Met Ser Gln Lys His
    50                  55                  60

Thr Glu Met Val Leu Glu Met Ser Ile Gly Ala Pro Glu Ala Gln Gln
65                  70                  75                  80

Arg Leu Ala Leu Ser Glu His Leu Val Thr Thr Ala Thr Phe Ser Ile
                85                  90                  95

Gly Ser Thr Gly Leu Val Val Tyr Asp Tyr Gln Gln Leu Leu Ile Ala
```

-continued

```
            100                 105                 110

Tyr Lys Pro Ala Pro Gly Thr Cys Cys Tyr Ile Met Lys Ile Ala Pro
        115                 120                 125

Glu Ser Ile Pro Ser Leu Glu Ala Leu Thr Arg Lys Val His Asn Phe
    130                 135                 140

Gln Ala Lys Pro Ala Val Pro Thr Ser Lys Leu Gly Gln Ala Glu Gly
145                 150                 155                 160

Arg Asp Ala Gly Ser Ala Pro Ser Gly Gly Asp Pro Ala Phe Leu Gly
                165                 170                 175

Met Ala Val Asn Thr Leu Cys Gly Glu Val Pro Leu Tyr Tyr Ile
            180                 185                 190


<210> SEQ ID NO 7
<211> LENGTH: 12
<212> TYPE: PRT
<213> ORGANISM: Homo sapiens

<400> SEQUENCE: 7

Leu Ile Lys Arg Ile Gln Ala Met Ile Pro Lys Gly
1               5                   10


<210> SEQ ID NO 8
<211> LENGTH: 10
<212> TYPE: PRT
<213> ORGANISM: Homo sapiens

<400> SEQUENCE: 8

Leu Leu Asp Thr Leu Leu Gly Arg Met Leu
1               5                   10


<210> SEQ ID NO 9
<211> LENGTH: 30
<212> TYPE: PRT
<213> ORGANISM: Homo sapiens

<400> SEQUENCE: 9

Cys Pro Val His Leu Lys Arg Leu Leu Ile Val Val Val Val Val Val
1               5                   10                  15

Leu Ile Val Val Val Ile Val Gly Ala Leu Leu Met Gly Leu
            20                  25                  30


<210> SEQ ID NO 10
<211> LENGTH: 20
<212> TYPE: PRT
<213> ORGANISM: Homo sapiens

<400> SEQUENCE: 10

Met Ala Glu Ser His Leu Leu Gln Trp Leu Leu Leu Leu Leu Pro Thr
1               5                   10                  15

Leu Cys Gly Pro
            20


<210> SEQ ID NO 11
<211> LENGTH: 9
<212> TYPE: PRT
<213> ORGANISM: Homo sapiens

<400> SEQUENCE: 11

Val Leu Pro Leu Lys Leu Leu Met Pro
1               5


<210> SEQ ID NO 12
```

<211> LENGTH: 9
<212> TYPE: PRT
<213> ORGANISM: Homo sapiens

<400> SEQUENCE: 12

Tyr Phe Pro Leu Val Ile Asp Tyr Phe
1 5

<210> SEQ ID NO 13
<211> LENGTH: 7
<212> TYPE: PRT
<213> ORGANISM: Homo sapiens

<400> SEQUENCE: 13

Ile Cys Met His Leu Gly Leu
1 5

<210> SEQ ID NO 14
<211> LENGTH: 15
<212> TYPE: PRT
<213> ORGANISM: Homo sapiens

<400> SEQUENCE: 14

Pro Leu Leu Asp Lys Leu Val Leu Pro Val Leu Pro Gly Ala Leu
1 5 10 15

<210> SEQ ID NO 15
<211> LENGTH: 79
<212> TYPE: PRT
<213> ORGANISM: Homo sapiens

<400> SEQUENCE: 15

Phe Pro Ile Pro Leu Pro Tyr Cys Trp Leu Cys Arg Ala Leu Ile Lys
1 5 10 15

Arg Ile Gln Ala Met Ile Pro Lys Gly Ala Leu Ala Val Ala Val Ala
20 25 30

Gln Val Cys Arg Val Val Pro Leu Val Ala Gly Gly Ile Cys Gln Cys
35 40 45

Leu Ala Glu Arg Tyr Ser Val Ile Leu Leu Asp Thr Leu Leu Gly Arg
50 55 60

Met Leu Pro Gln Leu Val Cys Arg Leu Val Leu Arg Cys Ser Met
65 70 75

<210> SEQ ID NO 16
<211> LENGTH: 26
<212> TYPE: PRT
<213> ORGANISM: Homo sapiens

<400> SEQUENCE: 16

Tyr Ser Val Ile Leu Leu Asp Thr Leu Leu Gly Arg Met Leu Pro Gln
1 5 10 15

Leu Val Cys Arg Leu Val Leu Arg Cys Ser
20 25

<210> SEQ ID NO 17
<211> LENGTH: 8
<212> TYPE: PRT
<213> ORGANISM: Homo sapiens

<400> SEQUENCE: 17

His Leu Cys Met Ser Val Thr Thr
1 5

-continued

```
<210> SEQ ID NO 18
<211> LENGTH: 14
<212> TYPE: PRT
<213> ORGANISM: Homo sapiens

<400> SEQUENCE: 18

Ile Pro Gln Ala Met Leu Gln Ala Cys Val Gly Ser Trp Leu
1               5                   10


<210> SEQ ID NO 19
<211> LENGTH: 8
<212> TYPE: PRT
<213> ORGANISM: Homo sapiens

<400> SEQUENCE: 19

Pro Gln Leu Leu Thr Leu Val Pro
1               5


<210> SEQ ID NO 20
<211> LENGTH: 24
<212> TYPE: PRT
<213> ORGANISM: Homo sapiens

<400> SEQUENCE: 20

Thr Thr Cys Gln Ala Leu Gly Val Cys Gly Thr Met Ser Ser Pro Leu
1               5                   10                  15

Gln Cys Ile His Ser Pro Asp Leu
            20


<210> SEQ ID NO 21
<211> LENGTH: 35
<212> TYPE: PRT
<213> ORGANISM: Homo sapiens

<400> SEQUENCE: 21

Phe Gly Ile Pro Cys Cys Pro Val His Leu Lys Arg Leu Leu Ile Val
1               5                   10                  15

Val Val Val Val Val Leu Ile Val Val Val Ile Val Gly Ala Leu Leu
            20                  25                  30

Met Gly Leu
        35
```

ANTIGEN-DRUG VEHICLE ENABLING TRANSMUCOSAL AND TRANSDERMAL ADMINISTRATION, AND METHOD OF INDUCING MUCOSAL IMMUNITY AND MUCOSAL VACCINE AND DDS USING THE SAME

This application is a U.S. national stage of International Application No. PCT/JP2005/005659 filed Mar. 22, 2005.

TECHNICAL FIELD

The present invention relates to an antigen-drug vehicle enabling transmucosal and transdermal administration, and more specifically, to a method of inducing mucosal immunity which causes preferential and effective, particularly selective production of an antigen-specific secretory immunoglobulin A, a mucosal vaccine, prevention or treatment of allergy, and a drug delivery system, which is characterized by using the vehicle for desired antigen or drug.

BACKGROUND ART

Conventional inactivated vaccine, toxoid, and the like are known to have the following drawbacks:

(1) Lack of Defense Against Infection in Natural Infection Route

The natural infection route of bacterial, virus, and the like is, for example, the mucosal membrane of the nasal cavity, the trachea, the intestinal tract, and the like, whereas the vaccine inoculation route is subcutaneous, intramuscular, and the like, which is different from the route described above. It is desired to achieve defense against infection by an inoculation route fit for the actual conditions of the natural infection, particularly defense against infection at the mucosal membrane from vaccine administration via the mucosal membrane.

(2) Low Mucosal Immunity

In the subject for vaccine inoculation, immunoglobulin G (hereinafter, simply referred to as “IgG” or “IgG antibody”) is mainly produced into the blood, and humoral immunity is induced. However, secretory immunoglobulin A (hereinafter, simply referred to as “IgA” or “IgA antibody”) which takes charge of mucosal immunity, is nearly not produced, and therefore, establishment of mucosal immunity is not expected. Furthermore, necessity and effectiveness of IgA antibody are as follows: IgA antibody plays a very important role in clinical immunity by taking charge of mucosal immunity, i.e., defense against infection at the mucosal membrane which is the entrance to infection onto the respiratory organs such as the nasal cavity and the trachea by spray or air, and infection onto the intestinal tract by oral. Furthermore, IgA antibody has cross immunity, i.e., cross-neutralization activity, and broad spectrum for infection defense as much, and also has defense against infection for variant antigen, whereas IgG antibody has high specificity for antigen, but has narrow spectrum for infection defense, leading to nearly not being effective for infection defense against variant antigen.

(3) Necessity of Additional Vaccination and Added Expense

Since IgG antibody is produced low only by one injection of the first immunization, and certain effects cannot be expected, it is required to increase blood IgG antibody value by additional inoculation, so-called booster inoculation of once or more times, based on the conditions of IgG antibody retention later. Therefore, repeated expense and effort are required, and on top of that, the case is often found where the chance of the booster inoculation is not effective for young children, especially infants two-years old or less, who is likely to depart from the chance of the booster inoculation, though the effects are recognized for the elderly, adults, and school children, who are benefited from the chance.

In other words, conventional inactivated vaccine, toxoid, and the like induces mainly production of blood IgG antibody in the subject for vaccine inoculation, and also brings actions and effects of increasing humoral immunity, being recognized for its efficacy. However, it has low performance of inducing IgA antibody production or mucosal immunity, showing the limit about sufficient function and effects for defense against natural infection. From such circumstances, there have been many trials from various sides so far to resolve the drawbacks of the conventional vaccines. For example, it includes improvement of the vaccine antigen in quality or quantity, experimental production of live vaccine replacing inactivated vaccine, development of new inoculation route, mucosal vaccine, and the like, screening of adjuvant, which elevates humoral immunity and cause maintenance thereof, development of mucosal immunity adjuvant, and the like. However, development of mucosal vaccine which is safe and effective has not been achieved.

Hereinafter, development of mucosal vaccine will be explained.

(1) Increase of the Amount of the Vaccine Antigen

A trial has been conducted of increasing the amount of the vaccine antigen which is inoculated subcutaneously or intramuscularly, or increasing the amount of IgG and IgA antibodies, which are secreted to the mucosal membrane. For example, a method wherein neuraminidase of the virus membrane protein is added to and mixed with conventional inactivated influenza vaccine to increase antibody production amount, or a method wherein MF59 is added and mixed as an adjuvant, and the like has been tried. However, these methods have been found to have disadvantages such as incurrence of pain, strong adverse reaction, and the like.

(2) Vaccine of Nasal Administration Type

A method has been tried wherein liquid split antigen is directly inoculated nasally for infection defense by IgA antibody, which is considered most effective, but the fact is pointed out that IgA production amount is small. In order to elevate IgA antibody production ability, there has been a trial that *Escherichia coli* heat-labile live toxin or cholera toxin is added to and mixed as an adjuvant with the split antigen to elevate mucosal immunity response, i.e., IgA antibody production ability. However, from the circumstances that the safety of the toxin as an adjuvant has been not proved, the trial treatment has been stopped, and not been put to practical use.

(3) Live Vaccine Using Cold-Attenuated Strain Which Can be Inoculated Into the Nasal Cavity A method is put to practical use wherein cold-attenuated influenza virus strain, which has optimal growth temperature of 25° C., and does not grow at 39° C., but the risk of toxicity recovery cannot be denied as the mechanism of attenuation of the parent cold-attenuated strain is not clear. In addition, since the active ingredient of the vaccine is a live virus, it has high invasion force into cells and excellent in initialization of immunity, but mild influenza symptoms often incur, so defects have been found that it cannot be used for human who has high risk of increase in severity when infected by influenza, elderly people, and the like.

(4) Other Vaccines

Developments of a vector vaccine which has vaccinia virus as a virus vector, attenuated live vaccine by reverse genetics, DNA vaccine which uses DNA or cDNA as an active ingredient, have been in progress in lab level, but not put to practical use.

Furthermore, development of immunity adjuvant will be explained below.

(1) Immunity Adjuvant

The immunity adjuvant is a general name of a substance which has regulation activity such as reinforcement or inhibition of immune response, and largely divided into two kinds: a substance which is related to a dosage form for the purpose of sustained-release, retention, and the like of antigen within the subject for inoculation, and a substance which helps elevation, inhibition, and the like of immune response. Between them, as the former, i.e., as the adjuvant for dosage form, for example, vaccine or toxoid with use of aluminum phosphate, alum, and the like has been already put to practical use. However, the latter, i.e., the adjuvant which helps reinforcement/elevation of immune response has not been known yet to be put to practical use. For example, BCG live bacteria derived from bacteria, BCG-CWS, endotoxin, glucan, and the like, synthesized MDP, levamisole, Poly I-Poly C, bestatin, and the like, and interferons such as cytokines, TNF, CSF, and the like have been known, but it is considered that guarantee for the safety and efficacy is needed for the practical use of them, by the reasons of insufficient effects, and the like for adjuvant diseases such as arthritis, chronic arthritic rheumatism, hyper-γ-globulinemia, anemia, and the like. In addition, a technique is known (Patent Document 1) using a pulmonary surfactant/protein derived from a higher animal as an adjuvant in order to enhance induction of humoral immunity, but it has not known to be put to practical use.

(2) Development of Adjuvant for Mucosal Immunity

Various adjuvants have been developed, for example, pertussis toxin B oligomer (Patent Document 2), cholera toxin (Patent Document 3), *Escherichia coli* heat-labile enterotoxin B subunit (LTB) (Patent Document 4), starch particles (Patent Document 5), cholera toxin B chain protein (CTB) (Patent Document 6), B subunit of verotoxin 1 (Patent Document 7), oligonucleotide (Patent Document 8), interleukin 12 (Non-Patent Document 1), and the like. However, they have not been put yet to practical use.

As described above, necessity has been recognized widely and deeply for replacement of the conventional vaccine which is inoculated subcutaneously, intramuscularly, and the like with a mucosal vaccine which induces production of IgA antibody in the mucosal membrane, which is a natural infection route of virus. Particularly, as a vaccine of next generation in the 21 century, so-called mucosal vaccine, which induces production of IgA antibody, and local immunity or mucosal immunity, is expected and hoped worldwide to be developed and put to practical use, but not yet achieved. The reason is considered to be in the fact that safe and effective adjuvant, which imparts the function of inducing production of IgA antibody, and local immunity or mucosal immunity to vaccine, has not specified or established.

Patent Document 1: JP-T-2002-521460
Patent Document 2: JP-A-3-135923
Patent Document 3: JP-T-10-500102
Patent Document 4: JP-T-2001-523729
Patent Document 5: JP-T-2002-50452
Patent Document 6: JP-A-2003-116385
Patent Document 7: JP-A-2003-50452
Patent Document 8: The pamphlet of PCT WO 00/20039
Non-Patent Document 1: pp. 4780-4788, vol. 71, 2003, Infection and Immunity
Non-Patent Document 2: pp. 2-11, vol. 10, 2004, Journal of neonatal Nursing
Non-Patent Document 3: pp. 9-14, vol. 74 (suppl. 1), 1998, Biology of the Neonate
Non-Patent Document 4: pp. 452-458, vol. 24, 2001, American Journal of Respiratory Cell and Molecular Biology

DISCLOSURE OF THE INVENTION

The present invention has the following objects: specifically, to impart the function of inducing production of IgA antibody, and local immunity or mucosal immunity; development of safe and effective technique therefor; conversion from conventional humoral immunity vaccine to safe and effective mucosal immunity vaccine; prevention and treatment of allergy; and establishment of transmucosal/transdermal drug delivery system (hereinafter, simply referred to as "DDS") for administration and transport of a drug via the mucosal membrane or skin.

As means to solve the objects, the present invention provides an antigen-drug vehicle enabling transmucosal and transdermal administration, and a method of inducing mucosal immunity which causes preferential and effective, particularly selective production of an antigen-specific secretory Immunoglobulin A, a mucosal vaccine, an agent for prevention or treatment of allergy, and a transmucosal or transdermal DDS, which is characterized by using the vehicle for desired antigen or drug.

Application or general use of the antigen-drug vehicle provided by the present invention, brings actualization and popularization of a mucosal vaccine against various infections, an agent for prevention or treatment of allergy, and a transmucosal or transdermal DDS. The mucosal vaccine, which is an immunity means fit for the actual conditions of the natural infection, exerts remarkably excellent infection defense effects as compared to the conventional vaccines. In addition, the nasal cavity-mucosal IgA induced by the antigen-drug vehicle, brings inactivation of allergen, which makes reduced sensitization possible. Furthermore, application of aforesaid DDS for various drugs reinforces and promotes preventive and/or therapeutic effects of drugs by transmucosal and transdermal administration. As a result, this invention highly improves medical treatment, health and hygiene of the whole mankind, and also is hopeful good news to those engaged in the field of medical treatment, health and hygiene of the world. In addition, it provides widely means of imparting function and performance which makes it possible transmucosal and transdermal administration, which is simple compared to injection, widely for a biological preparation containing conventional and future vaccine, toxoid, and the like, and various drugs.

BEST MODE FOR CARRYING OUT THE INVENTION

Figure 1:
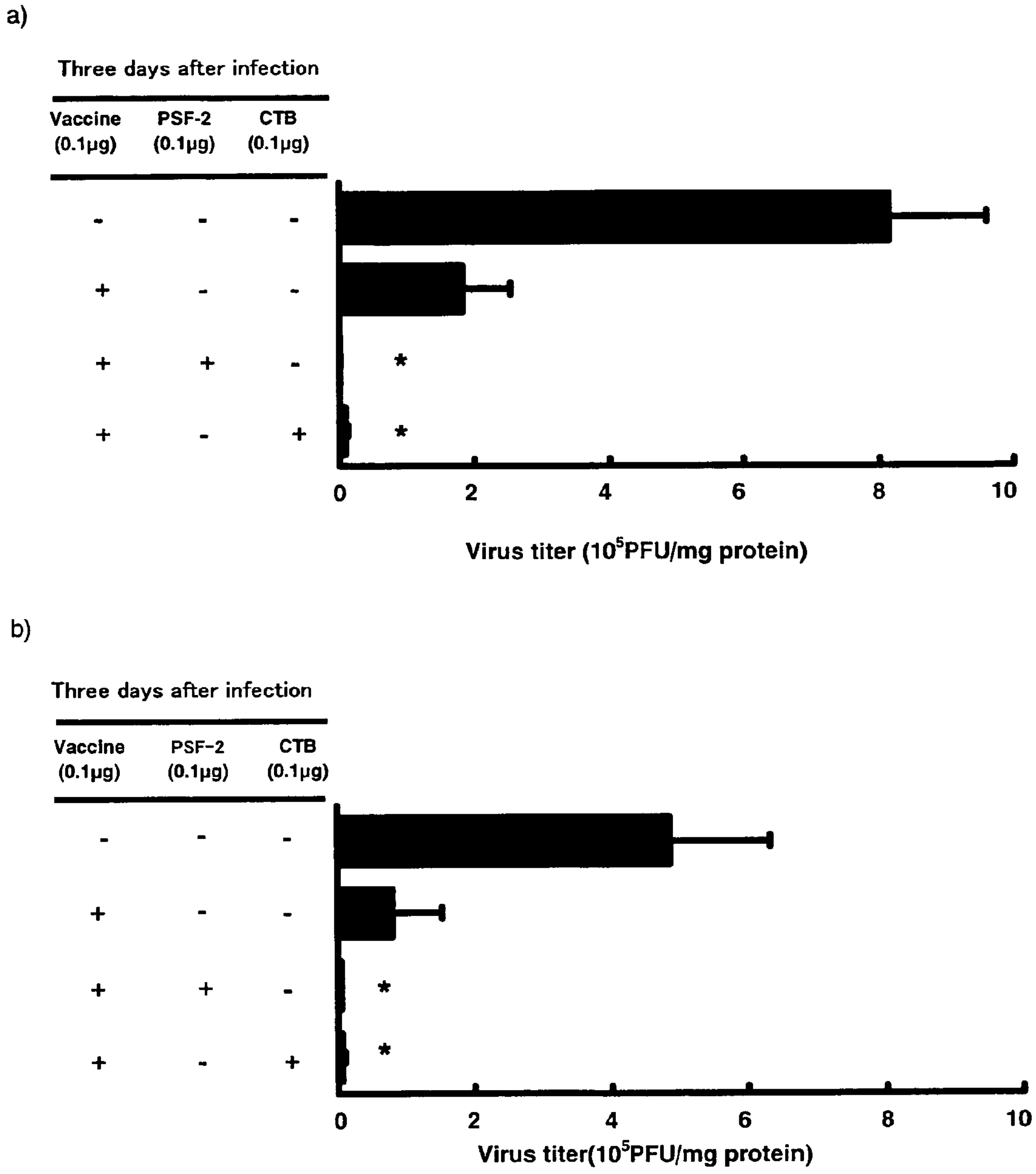
FIG. 1 represents inhibition effects of influenza virus infection in (c) the nasal cavity and (d) the alveoli in (a) the cavity and (b) the alveoli of various nasal influenza vaccine administrations, and subcutaneous-injection influenza vaccine administration. * represents the significance level from the group of vaccine-independent (without AD vehicle or adjuvant) administration by T-test ($p<0.01$). (Example 1)
Figure 1:
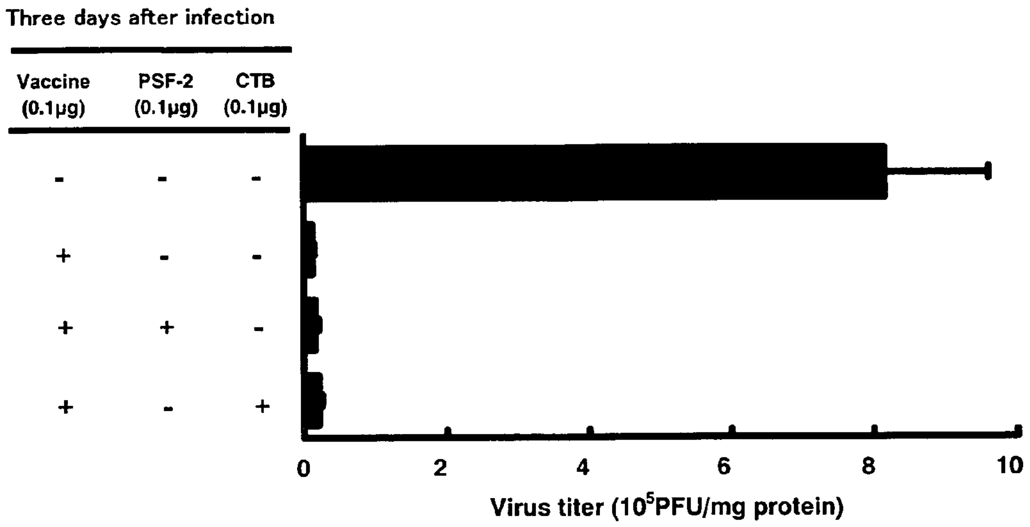
Figure 1:
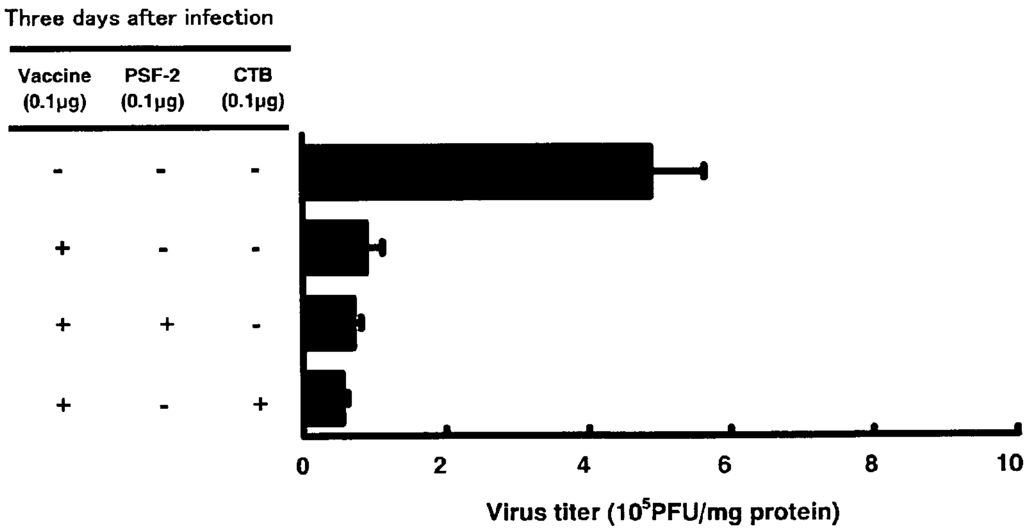

Embodiments of the present invention will be explained below.

1. Explanation for Terms and Ingredients of the Antigen-Drug Vehicle (1) Antigen-Drug Vehicle The vehicle (Antigen-drug vehicle, hereinafter, simply referred to as the "AD vehicle" or "ADV") is a complex of lipid and protein which is designed to enable transmucosal administration and transdermal administration of antigen, drug, and the like. The AD vehicle comprises (a) to (c) below.

(a) Pulmonary surfactant protein B or its fragment (including not only natural fragment obtained by protease, but also artificial fragment obtained by genetic engineering or peptide synthesis, or variant fragment by substitution and/or deletion of at least one amino acid constituting such fragment).

(b) Pulmonary surfactant protein C or its fragment (including not only natural fragment obtained by protease, but also artificial fragment obtained by genetic engineering or peptide synthesis, or variant fragment by substitution and/or deletion of at least one amino acid constituting such fragment).

(c) Lipid such as phospholipid and fatty acid. The shape and the structure is a membrane form (lipid membrane of sheet form or rolling form) retaining polypeptide chain of thorn shape or spike shape, which is a shape wherein the ends of the hydrophobic area of the multiple polypeptide chains are intrusive into the lipid membrane to be implanted in spike shape, and different from conventional lipid vesicle (liposome).

If desired antigen, drug, and the like is subjected to coexistence, contact, capture, adhesion or binding (riding) with the antigen-drug vehicle according to the present invention, it makes it possible transmucosal administration and transdermal administration of such antigen, drug, and the like. In other words, aforesaid vehicle is a ride of them, enabling transmucosal administration and transdermal administration of such antigen, drug, and the like.

In addition, ingredients of the AD vehicle, proteins, polypeptide, peptide or lipid used in preparation/production of the vehicle, i.e., pulmonary surfactant proteins B and C, a fragment thereof, a variant fragment by substitution and/or deletion of at least one amino acid constituting such fragment peptide, and the like, and lipid such as phospholipid, fatty acid, and the like will be explained in detail later.

(2) Pulmonary Surfactant

The pulmonary surfactant has been put to practical use from the middle 1990s in treatment of respiratory distress syndrome (RDS), and currently, various preparations derived from human, cattle, pig, and the like have been marketed widely to be in practical use (Non-Patent Document 2). In addition, synthetic peptide preparation containing active domain related to RDS treatment has been also marketed, and design development or synthesis of SP-B and SP-C analogues have been in progress (Non-Patent Document 3). Composition and constitution of the pulmonary surfactant are as follows: a complex comprising about 90% of lipid (67.3% of phosphatidyl choline, 19.3% of phosphatidylglycerol, 3.2% of phosphatidyl serine, and other free fatty acids, and the like), and about 10% of protein (surfactant proteins A, B, C and D: Hereinafter, simply referred to as "SP-A", "SP-B", "SP-C" and "SP-D", respectively). The molecular weight is 28 to 36 kDa for SP-A, 15 kDa for SP-B, 3.5 kDa for SP-C and 43 kDa for SP-D. SP-A and SP-D are hydrophilic (water-soluble) and lectin-like (membrane-associated). SP-B and SP-C are hydrophobic (lipid-soluble) and lipid-bindable, and has intrusion ability into phospholipid membrane and surfactant action. The pulmonary surfactant protein genes derived from human, cattle, pig, and the like are known, and for example, the accession number of full-length base sequence of human SP-B gene DNA is J02761, and that of human SP-C (and SP-C1) is J03890 in GenBank/NCBI (http//www.ncbi.nlm.nih.gov./). The coding region (CDR) of the human SP-B and SP-C obtained from NCBI and the amino acid sequence encoded by them, are described below.

SEQ ID No. 1: CDR base sequence of human SP-B gene DNA;

SEQ ID No. 2: Human SP-B full-length amino acid sequence interpreted from SEQ ID No. 1;

SEQ ID No. 3: CDR base sequence of human SP-C gene DNA;

SEQ ID No. 4: Human SP-C full-length amino acid sequence interpreted from SEQ ID No. 3;

SEQ ID No. 5: CDR base sequence of SP-C1 located on human SP-C gene DNA; and

SEQ ID No. 6: Human SP-C1 full-length amino acid sequence interpreted from SEQ ID No. 5.

(3) Protein or Peptide Used in This Invention

In preparation/production of the antigen-drug vehicle related to the present invention, combination of SP-B and SP-C, and combination of SP-B and SP-C1, which are derived from mammals such as human, cattle, pig, whale, dolphin, and the like, or fishes such as tunny, shark, ray, yellowtail, and the like, can be used respectively. For example, use can be also made of combination of SP-B and SP-C and combination of SP-B and SP-C1, which are human-derived proteins comprising the full-length amino-acid sequence described in SEQ ID Nos. 2, 4 and 6, respectively, can be used respectively. Furthermore, for example, use can be also made of hydrophobic (lipid-soluble) region of SP-B and SP-C based on the hydrophobicity value of Kyte-Doolittle and a fragment comprising the region, a variant fragment by substitution and/or deletion of at least one amino acid constituting such fragment peptide. For example, use can be made of natural peptide or peptide obtained by genetic engineering or chemical synthesis comprising the amino acid sequence described in SEQ ID Nos. 7 to 20, long chain peptide from them comprising such peptide, and a variant or synthetic analogue by substitution and/or deletion of at least one amino acid constituting such peptide. The amino acid number is represented by the ordinal number in the order from Met occupying the N-end of each sequence as first amino acid, toward the C-end direction (direction from the left to the right of the described sequences).

SEQ ID No. 7: Amino acid sequence of No. 214 to No. 225 of SEQ ID No. 2 (SP-B fragment);

SEQ ID No. 8: Amino acid sequence of No. 257 to No. 266 of SEQ ID No. 2 (SP-B fragment);

SEQ ID No. 9: Amino acid sequence of No. 29 to No. 58 of SEQ ID Nos. 4 and 6 (SP-C fragment);

SEQ ID No. 10: Amino acid sequence of No. 1 to No. 20 of SEQ ID No. 2 (SP-B fragment);

SEQ ID No. 11: Amino acid sequence of No. 102 to No. 110 of SEQ ID No. 2 (SP-B fragment);

SEQ ID No. 12: Amino acid sequence of No. 119 to No. 127 of SEQ ID No. 2 (SP-B fragment);

SEQ ID No. 13: Amino acid sequence of No. 136 to No. 142 of SEQ ID No. 2 (SP-B fragment);

SEQ ID No. 14: Amino acid sequence of No. 171 to No. 185 of SEQ ID No. 2 (SP-B fragment);

SEQ ID No. 15: Amino acid sequence of No. 201 to No. 279 of SEQ ID No. 2 (SP-B fragment);

SEQ ID No. 16: Amino acid sequence of No. 253 to No. 278 of SEQ ID No. 2 (SP-B fragment);

SEQ ID No. 17: Amino acid sequence of No. 300 to No. 307 of SEQ ID No. 2 (SP-B fragment);

SEQ ID No. 18: Amino acid sequence of No. 317 to No. 330 of SEQ ID No. 2 (SP-B fragment);

SEQ ID No. 19: Amino acid sequence of No. 344 to No. 351 of SEQ ID No. 2 (SP-B fragment);

SEQ ID No. 20: Amino acid sequence of No. 358 to No. 381 of SEQ ID No. 2 (SP-B fragment);

SEQ ID No. 21: Amino acid sequence of No. 24 to No. 58 of SEQ ID Nos. 4 and 6 (SP-C fragment).

According to the present invention, use can be made of combination of at least one kind selected from a group consisting of SP-Bs comprising the amino acid sequences described in SEQ ID Nos. 2, 7, 8 and 10 to 20, and a fragment thereof, and at least one kind selected from a group consisting of SP-Cs (and SP-C1) comprising the amino acid sequences described in SEQ ID Nos. 4, 6, 9 and 21, and a fragment thereof.

(4) Lipid Used in the Present Invention

As the phospholipid, phospholipid containing the pulmonary surfactant, for example, phosphatidyl choline (lecithin), dipalmitoyl phosphatidyl choline, phosphatidyl serine, and the like is preferably used. Additionally, use can be made of dipalmitoyl glycerophosphocholine, diacyl glycerophosphoglycerol, phosphatidylglycerol (cardiolipine), dilauroyl phosphatidylglycerol, dimiristoyl phosphatidylglycerol, dipalmitoyl phosphatidylglycerol, distearoyl phosphatidylglycerol, phosphatidyl inositol, phosphatidyl ethanolamine, phosphatidic acid, sphingomyelin, and the like. In addition, as the fatty acid, use can be made of lauric acid, myristic acid, palmitic acid, stearic acid, palmitoleic acid, oleic acid, and the like. In addition, use can be made of lipid derived from aquatic animal such as whale, tunny, dolphin, and the like, which has active pulmonary expansion.

(5) The Pulmonary Surfactant Preparations in the Market for RDS Treatment

According to the present invention, the pulmonary surfactant preparations in the market, for example, Surfacten (trademark), Infasurf, Curosurf, Humansurf, Exosurf, Alveofact, and the like can be used as the AD vehicle, which have been approved by the relevant authority for the safety and efficacy as a RDS treatment drug, and contains hydrophobic or lipid-soluble SP-B and SP-C and phospholipid. In addition to SP-B and SP-C, the marketed preparations containing hydrophilic or water-soluble SP-A and SP-D can be given to use after extracting the water-soluble proteins SP-A and SP-D with 1-butanol, and the like, and removing them to the detection limit or less. In addition, use of dry preparation is more desirable than liquid preparation considering the adjustment of the concentration to be used in preparation of the AD vehicle.

2. Novel Findings as a Base for the Present Invention

Under such very strict background techniques, this invention is made by keen observation and analysis of the present inventors from trial and error repeated over about 10 years, and profound knowledge and experience and novel idea, and it is based on the following astonishing findings.

(1) Conventional adjuvant reinforces antigen presenting-performance by causing inflammation, and originally there are four kinds of protein active ingredients, SP-A, SP-B, SP-C and SP-D, which are surfactants secreted by pulmonary or intestinal tract mucosal membrane. It has been found that if virus antigen is subjected to coexistence, contact, capture or adsorption with a complex of the combination of SP-B and SP-C excluding SP-A and SP-D, and phospholipid, or a complex of the combination of synthetic peptides of both fragments of SP-B and SP-C comprising lipid-soluble region thereof (active region), and lipid membrane (aforesaid AD vehicle), the antigen-presenting cells in the mucosal membrane of the nasal cavity are activated without causing inflammation, virus antigens are incorporated into the cells in good efficiency, and also anti-virus IgA production by the mucosal membrane is induced effectively and preferentially, and further selectively without causing induction of IgG production in the mucosal membrane or blood.

(2) In addition, it has been found that by adding to and mixing a complex of the combination of SP-B and SP-C, and phospholipid, or a complex of the combination of synthetic peptides of both fragments of SP-B and SP-C comprising lipid-soluble region thereof (active region), and lipid membrane (aforesaid AD vehicle), with influenza virus split antigen which is used as safe inactivated vaccine antigen conventionally, selective induction of secretory IgA production is achieved with the activation of the antigen-presenting cells sufficiently reinforced and supplemented, which is poor in independent split antigen compared with live vaccine, while maintaining high safety of the split antigen.

3. Process of Completing the Above-Mentioned Findings (1) The present inventors have studied extensively to elucidate the mechanism of the development of influenza, and a treatment and prevention method for influenza. During the process, it has been elucidated that pulmonary surfactant adsorbs and inactivates tryptase clara of hemagglutinin (HA) processing protease of the respiratory tract, which manifests virus membrane infusion activity and infectious ability by restrictive cleavage of HA of the influenza virus membrane protein, resulting in inhibiting the growth cycle of the virus.

(2) As a result of continuous study, it has been found that in addition to the actions described above, the pulmonary surfactant selectively activates mucosal antigen-presenting cells, and thus activates immunity performance against virus antigen, leading to induction of secretory IgA, but not leading to induction of IgG. Furthermore, it has been shown that SP-B and SP-C are important as well as the lipid ingredient, as active ingredients reinforcing mucosal immunity in the pulmonary surfactant. The active region of these protein ingredients has been specified, and the efficacy of mucosal immunity reinforcement has been evaluated.

(3) Furthermore, studies have been progressed in view of a biological defense substance in the mucosal membrane of the respiratory tract, and defense against virus infection as described above, and it has been proved that the pulmonary surfactant, which is secreted in the living body, is involved in selective induction of IgA production as mucosal immunity adjuvant derived from the living body.

(4) Studies have continued giving attention to the fact that (a) the pulmonary surfactant, which is originally physiologically active substance in the living body, has property of adsorbing specific bio-substance (Kido H., et al. FEBS Lett. Pulmonary surfactant is a potential endogenous inhibitor of proteolytic activation of Sendai virus and influenza A virus, 322 (29), 115-119, 1992), (b) the pulmonary surfactant is secreted from alveolar type II cell or clara cell, and then selectively incorporated into macrophage (Akira Suwabe, J. Jpn. Med. Soc. Biol. Interface; Surfactant metabolism disorder in alveolar proteinemia, 33, 10-13, 2002), and (c) the pulmonary surfactant is incorporated and metabolized in analogous cells, for example, antigen-presenting cells (dentritic cells).

As a result, it has been found that only SP-B and SP-C among the protein ingredients, and lipid ingredients of the pulmonary surfactant, function as the "AD vehicle" of mucosal vaccine which selectively induces IgA production, and that the active ingredient region of SP-B or active domain of mucosal immunity induction is a peptide comprising the following amino acid sequences:

```
SP-B 214-225:
                                        (SEQ ID No. 7)
Leu Ile Lys Arg Ile Gln Ala Met Ile Pro Lys Gly;
and

SP-B 257-266:
                                        (SEQ ID No. 8)
Leu Leu Asp Thr Leu Leu Gly Arg Met Leu.
```

In addition, it has been found that the active ingredient region of SP-C or active domain of mucosal immunity induction is a peptide comprising the following amino acid sequences:

```
SP-C 29-58:
                                        (SEQ ID No. 9)
Cys Pro Val His Leu Lys Arg Leu Leu Ile Val Val

Val Val Val Val Leu Ile Val Val Val Ile Val Gly

Ala Leu Leu Met Gly Leu.
```

(5) In addition, it has been found as the mechanism of selective IgA induction that the active ingredients of the pulmonary surfactant effectively conduct antigen presentation of T-lymphocyte by inducing increased expression of MHC Class II, CD40 and B7-2 of antigen-presenting dendritic cells, and in addition, promote class switch to IgA-producing B-lymphocyte by inducing cytokine TGF-β1 of a local mucosal membrane.

4. The Objects of the Present Invention Completed Based on the Findings and the Details Described Above are as Follows:

(1) The first object is to establish a mucosal immunity method. By providing the "AD vehicle" and using it, the present invention achieves selective induction of production of antigen-specific IgA, which is an active substance of mucosal immunity, and also establishes induction of safe and effective (with no adverse effects) mucosal immunity, and a method thereof.

(2) The second object is to improve qualities related to safety, efficacy and uniformity of the AD vehicle by use of a synthetic peptide. The present invention provides a complex (the AD vehicle), which is prepared with a synthetic peptide of active domain of SP-B mucosal immunity induction (comprising each amino acid sequence of SP-B 214-225 and SP-B 257-266 described above), a synthetic peptide of active domain of SP-C mucosal immunity induction (comprising each amino acid sequence of SP-C 29-58 described above), a synthetic analogue thereof, a long-chain synthetic peptide comprising these amino acid sequence as a part, and the like, and a lipid ingredient of the pulmonary surfactant, and improves the quality of the AD vehicle.

(3) The third object is conversion of conventional subcutaneous inoculation of vaccine to mucosal administration. The present invention employs the AD vehicle in inactivated vaccine of respiratory tract-infection virus, for example, inactivated vaccine of influenza, SARS, the measles, rubella, mumps, and the like, and inactivated vaccine of intestinal tract-infection virus, for example, inactivated vaccine of rotavirus, poliovirus, and the like, and converts subcutaneous inoculation vaccine thereof to mucosal vaccine.

(4) The fourth object is to provide a method of using the AD vehicle in inactivated vaccine against virus infection via mucosal membrane except for the respiratory tract and the intestinal tract, for example, inactivated vaccine against AIDS, Type B hepatitis, Type C hepatitis, and the like.

(5) The fifth object is to provide a method of using the AD vehicle in DNA vaccine, live vaccine, prevention and treatment of allergy, and the like.

(6) The sixth object is to provide a method of using the AD vehicle in transdermal inoculation (application, pasting, and the like) as an immunity route which can induce IgA besides the mucosal membrane.

(7) The seventh object is to open a way of use and application of the AD vehicle in agriculture, fishery, and the like, not only in DDS or pharmaceutics.

The AD vehicle provided by the present invention, has different performances and actions from adjuvants which have been used conventionally in immunology as follows: Specifically, conventional adjuvants are inoculated usually subcutaneously or intramuscularly, causing local inflammation reaction and attracting antigen-presenting cells or B- and T-lymphocytes, and has a foreign substance exerting its ability as active ingredient. In addition, they are used in combination with mineral oil or metal salt causing sustained-release and retention of antigen to maintain inflammation reaction over long time. In addition, those known as conventional mucosal vaccine/adjuvants are as described above, and a foreign substance such as *Escherichia coli* heat-labile live toxin and cholera toxin, and has risk of causing harmful actions or adverse actions. On the contrary, the AD vehicle according to the present invention, causes no local inflammation reaction. In addition, the AD vehicle is derived from biological ingredient, and on top of that, it is limited to active ingredient in the pulmonary surfactant or an active domain thereof, and uses low-molecular-weight peptide comprising such domain or domain region to achieve effective mucosal vaccine. Accordingly, the AD vehicle is very safe and non-invasive.

5. According to the Present Invention, Following (1) to (5) are Provided, Respectively.

(1) An antigen-drug vehicle, which is a complex comprising at least one fragment selected from pulmonary surfactant protein B or multiple fragments derived from the protein B, at least one fragment selected from pulmonary surfactant protein C or multiple fragments derived from the protein C, and at least one lipid.

More specifically, the AD vehicle is a complex comprising at least three substances in total, which are selected by at least one kind from each group of following Group I (group of pulmonary surfactant protein B, and natural and synthetic polypeptide derived or originated from the protein B), Group II (group of pulmonary surfactant protein C, and natural and synthetic polypeptide derived or originated from the protein C) and Group III (group of lipid such as phospholipid, fatty acid, and the like).

[Group I] Pulmonary surfactant protein B and a polypeptide comprising following amino acid sequence described in SEQ ID No. 2 (The amino acid number is assigned in the order from Met occupying the N-end of each sequence as first amino acid, toward the C-end): Nos. 1 to 381 (SEQ ID No. 2), Nos. 214 to 225 (SEQ ID No. 7), Nos. 257 to 266 (SEQ ID No. 8), Nos. 1 to 20 (SEQ ID No. 10), Nos. 102 to 110 (SEQ ID No. 11), Nos. 119 to 127 (SEQ ID No. 12), Nos. 136 t 142 (SEQ ID No. 13), Nos. 171-185 (SEQ ID No. 14), Nos. 201-279 (SEQ ID No. 15), Nos. 253-278 (SEQ ID No. 16), Nos. 300-307 (SEQ ID No. 17), Nos. 317-330 (SEQ ID No. 18), Nos. 344-351 (SEQ ID No. 19), NOs. 358-381 (SEQ ID No. 20), a polypeptide comprising at least one sequence of the above-mentioned amino acid sequences as an active domain, a polypeptide by substitution and/or deletion of at least one amino acid in the above-mentioned amino acid sequences, a synthetic analogue thereof, a modified body thereof by saccharide or saccharide chain, and the like.

[Group II] Pulmonary surfactant protein C and a polypeptide comprising following amino acid sequence described in SEQ ID No. 4 (The amino acid number is assigned in the order from Met occupying the N-end of each sequence as first amino acid, toward the C-end): Nos. 1 to 197 (SEQ ID No. 4), Nos. 29 to 58 (SEQ ID No. 9), Nos. 24 to 58 (SEQ ID No. 21), a polypeptide comprising the amino acid sequence of Nos. 1 to 191 of SEQ ID No. 6, a polypeptide comprising at least one sequence of the above-mentioned amino acid sequences as an active domain, a polypeptide by substitution and/or deletion of at least one amino acid in the above-mentioned amino acid sequences, a synthetic analogue thereof, a modified body thereof by saccharide or saccharide chain, and the like.

[Group III] Lipid such as phospholipid like phosphatidyl choline, dipalmitoyl phosphatidyl choline, phosphatidyl serine, dipalmitoyl glycerophosphocholine, diacyl glycerophosphoglycerol, phosphatidylglycerol, phosphatidyl inositol, phosphatidyl ethanolamine, phosphatidic acid, and the like, fatty acid like lauric acid, myristic acid, palmitic acid, stearic acid, oleic acid, and the like, and the like.

In addition, the antigen-drug vehicle preferably has a shape and structure wherein the above-mentioned Group III is a lipid membrane of sheet form or rolling form, and multiple chains of each of the above-mentioned Group I and Group II are implanted in spike shape with the hydrophobic area ends being intrusive into the lipid membrane.

(2) A mucosal vaccine which is characterized by induction of mucosal immunity, which is obtained by subjecting the antigen-drug vehicle of the above-mentioned (1) to coexistence, contact, capture or adsorption with antigen.

(3) An agent for prevention and treatment of allergy which is characterized by induction of mucosal immunity, which is obtained by subjecting the antigen-drug vehicle of the above-mentioned (1) to coexistence, contact, capture or adsorption with allergen. The action and effects are by deactivation or reduced sensitization of allergen such as cedar pollen coming by air and sucked, tick, and the like, by mucosal IgA in the nasal cavity or the nasal pharynx.

(4) A transmucosal and/or transdermal DDS which is obtained by subjecting the antigen-drug vehicle of the above-mentioned (1) to coexistence, contact, capture or adsorption with a drug in an effective amount.

(5) A method of inducing mucosal immunity which is characterized by administering a mucosal vaccine, which is obtained by subjecting the antigen-drug vehicle of the above-mentioned (1) to coexistence, contact, capture or adsorption with antigen, into the nose or upper respiratory tract.

The induction of mucosal immunity in the inventions of the above-mentioned (2), (3) and (5) is preferably characterized by promoting the production of an IgA antibody in a local mucosal membrane, and further by promoting the production of TGF-β1 and Th2-type cytokine in the local mucosal membrane.

6. Hereinafter, Embodiments of the Present Invention Will be Explained.

(1) Composition of the AD Vehicle

Followings are dry wt. % of the three groups of the above-mentioned Group I (group of pulmonary surfactant protein B, and natural and synthetic polypeptide derived or originated from the protein B), Group II (group of pulmonary surfactant protein C, and natural and synthetic polypeptide derived or originated from the protein C) and Group III (group of lipid such as phospholipid, fatty acid, and the like): about 0.1 to about 6.0 wt. % of Group I, about 0.1 to about 6.0 wt. % of Group II and about 88 to about 99.8 wt. % of Group IIII. In preparation of the antigen-drug vehicle, the composition is adjusted to Group I %+Group II %+Group III %=100% by wt. %.

(2) Preparation of the AD Vehicle

Preparation procedures are as follows, for example: 2 mg of Group I, 2 mg of Group II and 96 mg of Group III are weighed, respectively (Group I %+Group II %+Group III %=100% by wt. %), which are suspended uniformly in 5 ml isotonic solution, for example, physiological saline solution or phosphate buffered saline (PBS). Resultant suspension is given to use as a solution of the antigen-drug vehicle (100 mg/5 ml). The vehicle is prepared in each use. For suspension, ultrasonic wave, homogenizer, mixer, shaker, and the like can be used. The ultrasonic wave is likely to cause liquid change (increase of viscosity) by excessive treatment, and thus, a mixer, for example, box mixer (e.g., Vortex mixer (trademark)) is preferably used.

For specification of 96 mg of the lipid of Group III, for example, a mixture of 71 mg of phosphatidyl choline, 21 mg of phosphatidylglycerol and 4 mg of phosphatidyl serine, and the like can be adopted (the total of the lipid amount is 96 mg). In addition, in case of using marketed pulmonary surfactant preparation for RDS treatment, which is ensured to contain SP-B and SP-C excluding SP-A and SP-D, the suspension prepared in accordance to the instruction manual, can be given to use as it is or as a solution of the antigen-drug vehicle.

(3) Preparation of Mucosal Vaccine

A mucosal vaccine is prepared by adding to and mixing the solution of the antigen-drug vehicle with an undiluted vaccine solution that the dry-weight ratio of the amount of the antigen-drug vehicle (V) to the amount of antigen in the vaccine (A) becomes about 0.2 to about 5. For example, if the antigen content is 1 μg/ml in 1,000 ml of the vaccine undiluted solution, and the weight ratio adopted is A/V=1, the addition and mixing amount of the solution of the antigen-drug vehicle (100 mg/5 ml), which has been prepared in the above-mentioned (2), is 50 μl. For uniform mixing, homogenizer, mixer, shaker, stirrer, and the like can be used.

(4) Preparation of Transmucosal or Transdermal DDS

The transmucosal or transdermal DDS can be prepared by using a drug instead of an antigen in the same manner as in the above-mentioned (3).

EXAMPLES

Hereinafter, the constitution and effects of the present invention will be explained in detail by showing Examples. However, this invention is not limited only to these examples, explanation and description.

Raw materials, experimental procedures, and the like used in these examples are as follows.

(1) Pulmonary Surfactant

The pulmonary surfactant used as the "antigen-drug vehicle (the AD vehicle) is a sample prepared from bovine lung by the method of Howgood, et al. (PSF-1) (Howgood S, et al.,: Effects of a surfactant-associated protein and calcium ions on the structure and surface activity of lung surfactant lipids. Biochemistry, 24, 184-190, 1985), or largely a sample prepared by extracting the former sample with 1-butanol to remove water-soluble protein ingredients, SP-A and SP-D, or reduce them to detection limit or less (PSF-2) (Haagasman H P, et al.,: The major lung surfactant protein, SP28-36, is a calcium-dependent, carbohydrate binding protein, J. Biol. Chem. 262, 13977-13880, 1987), and further any synthetic peptide of the active regions of the lipid-soluble proteins, SP-B or SP-C, which contains 40 wt. % or more to the whole of phospholipid comprising mainly phosphatidyl choline and dipalmitoyl phosphatidyl choline, and further contains 10 to 20% of phosphatidylglycerol and 2 to 5% of phosphatidyl serine, which are similar to the pulmonary surfactant lipid, or a sample containing 0 to 3.5% of both peptides in combination. Among these samples, investigated were a sample containing both peptides in combination of the active regions of SP-B and SP-C (PSF-3), a sample containing a synthetic peptide of the active region of SP-B (PSF-4) and a sample containing a synthetic peptide of the active region of SP-C (PSF-5). Alternatively, known samples corresponding to PSF-1 or PSF-2, for example, Survanta, Infasurf, Curosurf, Humansurf, Exosurf, Alveofact, and the like (trademark) are also used.

(2) Animal 6 week-old female BALB/c mouse, and 10 week-old Hartley guinea pig were purchased from Japan SLC, Inc. (Shizuoka, Japan) and used. All of the animal experiments were conducted in the cage for infected animals (P2 level) of the experimental animal center of the medical faculty of University of Tokushima, and conducted in accordance of the guideline of the animal experiment committee of the medical faculty of University of Tokushima.

(3) Preparation of Split-Type Influenza Vaccine

Preparation of split-type influenza vaccine was conducted with the following procedures using the suspension derived from a grown egg where the influenza virus, A Aichi/68/2/H3N2 strain was inoculated ($1\times10^8$ Plaque forming unit [PFU]) (supplied by Professor Masanobu Ouchi in microbiology class of Kawasaki medical school). P-propiolactone (Wako Pure Chemical Industries, Ltd., Osaka, Japan) was added to the virus suspension, which was dialyzed in 0.004 M PBS (TakaraBio, Inc., Shiga, Tokyo, Japan) overnight, to 0.05% of the liquid amount and 8 nM of the final concentration, and incubated for 18 hours in an ice bath. Then, it was incubated for 1.5 hours at 37° C. to hydrolyze the β-propiolactone. Then, Tween 20 (Wako Pure Chemical Industries, Ltd.) was added to 0.1% of the final concentration, and diethylether (Wako Pure Chemical Industries, Ltd.) was further added in the equal amount to that of Tween, and mixed with shaking for two hours at 4° C. This solution was centrifuged at 2,000 rpm for 5 minutes to collect the aqueous layer. Furthermore, removal of diethylether was conducted from the aqueous layer with Automatic Environmental SpeedVac System (SAVANT INSTRUMENTS, INC., New York, USA). This was filtered with a 0.45 μm filter (MILLIPORE, Massachusetts, USA), to prepare inactivated split-type influenza vaccine.

(4) Immunization

To the split-type influenza vaccine prepared by the production method described above were mixed and used the above-mentioned pulmonary surfactant (PSF-1), 1-butanol extracted pulmonary surfactant (PSF-2), the synthetic peptides of the active regions of SP-B and SP-C and the pulmonary surfactant lipid (PSF-3, -4 and -5), known pulmonary surfactant product, or cholera toxin B subunit (CTB, SIGMA, Missouri, USA) as an immune adjuvant. The pulmonary surfactant or the corresponding sample described above was suspended in PBS in situ at a concentration required in vaccine administration, and treated with ultrasonic wave for 5 minutes at room temperature to give a uniform suspension. To this was added 0.1 μg of the split-type influenza vaccine to 0.1 μg by dry weight of the pulmonary surfactant or the corresponding sample, and mixed in a vortex mixer, and left for 1 hour at room temperature to be used. CTB was adjusted in situ in the similar manner, and mixed in 0.1 μg to 0.1 μg of the split-type influenza vaccine (Watanabe I, et al.,: Characterization of protective immune responses induced by nasal influenza vaccine containing mutant cholera toxin as a safe Adjuvant (CT112K). Vaccine 2002; 20: 3443-55).

For nasal administration of the vaccine, the above-mentioned adjusted product was diluted in PBS to be a 0.1 μg/1 μl solution of Phosphate buffered saline (PBS), and this was administered to both sides by 1 μl, respectively per one animal and 2 μl in total was nasal-administered to both sides of the nasal cavities of the mouse anesthetized with ether. For conventional subcutaneous injection, which was conducted for comparison, the split-type influenza vaccine was diluted in PBS to be a solution of 0.1 μg/50 μl, and this was administered to the hypoderma of the mouse neck. For the control group, PBS was administered in the same amount as that of the vaccine solution. After 4 weeks, second immunization was carried out in the same manner as the first immunization, and two weeks after the second immunization, the washing solutions of the nasal cavity and the alveoli, and the serum of the mouse, were prepared, which were used in measurement of virus-specific IgA and IgG, and virus infection experiment.

(5) Preparation of the Washing Solutions of the Nasal Cavity and the Alveoli, and the Serum of the Mouse The vaccine-administered mouse was cut open in the abdomen and the chest under pentobarbital anesthesia, and the trachea was cut open, and Atom venous catheter tapered 3 Fr (Atom medical Corporation, Tokyo, Japan) was inserted into the lung, and 1 ml of physiological saline solution was infused, and this solution was collected. This was repeated three times, and the collected solution, 3 ml in total was used as the washing solution of the alveoli. After collecting the washing solution of the alveoli, the atom vein catheter was inserted from the opened trachea to the direction of the nasal cavity, and 1 ml of physiological saline solution was infused, and the solution coming from the nose was collected. This solution was used as the washing solution of the nose. Furthermore, blood collecting was conducted from the heart, and the serum was prepared by centrifuge at 5,000 rpm for 10 minutes.

(6) Quantitization of Protein

The protein content in the washing solutions of the nose and the lung, and the serum was measured with BCA Protein Assay Reagent Kit (PIERCE, Illinois, USA) (Smith P K., et al.,: Measurement of protein using bicinchoninic acid. Anal. Biochem., 150, 76-85, 1985). Absorbance at 562 nm was measured with SPECTRAmax PLUS 384 (Molecular Devices Corporation, California, USA).

(7) Experiment for Virus Infection and Evaluation for Infection Value.

The influenza virus strain, A Aichi/68/2/H3N2 strain, which is the same as the virus strain used in the preparation of the split-type influenza vaccine, was used in infection. Two weeks after completion of the second immunization, the mouse was anesthetized with ether, and a suspension derived from an egg where the influenza virus was grown, was dropped for infection into both sides of the nasal cavities in $7\times10^4$ PFU/3 μl. 3 weeks after the infection, the washing solutions of the nasal cavity and the alveoli were prepared in the same manner as described above, which were used in evaluation of virus infection value. The evaluation of virus infection value was conducted using A 549 cells (supplied by Professor Masanobu Ouchi in microbiology class of Kawasaki medical school). A 549 cells were incubated under the condition of 5% bovine fetal serum/DMEM (Gibco, New York, USA). A 549 cells were subcultured to be 100% confluent in 6 well-incubation plate (Greiner Deutsche Stuttgart), and changed to no-serum medium after 24 hours. The washing solutions of the nasal cavity and the alveoli of influenza infection mouse were dropped in 500 μl, respectively to each well, and incubated in $CO_2$ incubator at 37° C. for 12 hours to 16 hours. To this was added the 1% PBS solution of erythrocyte, which was collected from the guinea pig, and the mixture was left for 5 minutes at room temperature. The mixture was washed with 1 mM $Ca^{2+}/Mg^{2+}$ PBS, and evaluation of virus infection value was conducted by counting the cell agglutinating erythrocyte as a virus infection cell (Tashiro M., Homma M.: Pneumotropism of Sendai virus in relation to protease-mediated activation in mouse lungs. Infect. Immun. 39, 879-888, 1983).

(8) Purification of Anti-Influenza Specific IgA and IgG

Purification of anti-influenza specific IgA and IgG was conducted as follows to be used as standard for quantitization in ELISA assay. IgG fractions were purified from the lung-washing solutions of the influenza vaccine-administered and virus-infected mice by affinity chromatography with recombinant *E. coli* expression Protein G cephalose 4B column (ZYMED LABORTORIES INC, San Francisco, USA). Anti-mouse IgA goat IgG (SIGMA) was bound to BrCN-activated cephalose 4B column (Amersham Bioscience, New Jersey, USA), and using this, IgA fractions were purified by affinity chromatography from the Protein G passing-through fraction. To purify virus-specific antibody from these IgG and IgA fractions, inactivated split-type influenza vaccine used in immunization was bound to BrCN activated cephalose column, and anti-influenza specific IgA and IgG were purified, respectively by antigen affinity chromatography from the IgG and IgA fractions using this. Coupling of the split-type influenza protein as a ligand to the column was carried out by the binding reaction with 0.1 M $NaHCO_3$/0.5 M NaCl buffer solution (pH 8.5), and removing the free ligand with 0.1 M acetic acid/0.5 M NaCl buffer solution (pH 8.5) and neutralizing by PBS (pH 7.5). After affinity-binding reaction by PBS (pH 7.5) and removal of free antibody, each of the affinity chromatography was subjected to elution of the specific antibody by glycine-HCl buffer solution (pH 2.8). Eluted fractions were neutralized immediately by 0.5 M Tris HCl buffer solution (pH 9.0), and dialyzed with MilliQ water and lyophilized, which was used as dissolved in PBS in situ.

(9) Quantitization of Anti-Influenza Antibody

Contents of anti-influenza IgA and IgG in the washing solutions of the nasal cavity and the alveoli, and the serum, were quantitized by ELISA assay. The ELISA assay was carried out according to the method of Mouse ELISA Quantitization kit of BETHYL LABORATORIES (Texas, USA). To each well of 96 well Nunc immunoplate (Nalgen Nunc International, New York, USA), 1 μg of the vaccine and 100 μl of 1 μg/ml PBS solution of bovine serum albumin (BSA, SIGMA, Missouri, USA) were added, and reaction for layer-solidification was conducted at 4° C. overnight. Then, each well was washed three times with the washing solution (50 mM Tris, 0.14 M NaCl, 0.05% Tween 20, pH 8.0) to remove the vaccine solution. To each well was added 50 mM Tris-HCl buffer solution containing 0.15 M NaCl and 1% BSA, and the blocking reaction was carried out at room temperature for 1 hour. Each well was washed three times with the washing solution, and then added were 100 μl of the washing solutions of the nasal cavity and the alveoli, and the serum, which had been diluted with a suitable amount of a sample-binding buffer solution (50 mM Tris, 0.15 M NaCl, 1% BSA, 0.05% Tween 20, pH 8.0), and the mixture was left for reaction at room temperature for 2 hours. Color reaction was conducted with TMB Microwell Peroxidase Substrate System (Kirkegaard & Perry Laboratories, Inc. Maryland, USA), using Goat anti-mouse IgA or IgG-horse rADish peroxidase (HRP) (BETHYL LABORATORIES INC.) as secondary antibody. The reaction was terminated by adding 100 μl of 2 M $H_2SO_4$ (Wako Pure Chemical Industries, Ltd.) to each well, and absorbance at 450 nm was measured with SPECTRAmax PLUS 384. Anti-influenza 10 ng of IgA and IgG purified from the above-mentioned lung-washing solution was treated in the same manner as a standard for quantitization, and obtained absorbance was used.

(10) Preparation of Dendritic Cells and Flow Cytometry

Preparation of dendritic cells was carried out from the nose, lung and spleen collected from the mice of each group (4 in one group) 2 days after the first immunization, by the method of Gonzalez-Juarrero M (Gonzalez-Juarrero M, Orme I M.: Characterization of murine lung dendritic cells infected with Mycobacterium tuberculosis. Infect Immun. 2001; 69: 1127-33). Preparation of dendritic cells from the nose and collagenase treatment therefor was conduced according to the method of Asanuma H, et al. (Asanuma H, et al.,: Characterization of mouse nasal lymphocytes isolated by enzymatic extraction with collagenase. J. Immunol. Methods 1995; 187: 41-51). The dendritic cells prepared from each of the tissues, were washed with 1 mM EDTA/PBS, and added per $10^6$ cells were each 1 μg/ml of FITC conjugated Anti-IA/IE (MHC class II) and PE conjugated Anti CD40 or FITC conjugated Anti-CD80 (B7-1) and PE conjugated Anti CD86 (B7-2) (BD Bioscience, New Jersey, USA), and left for reaction for 30 minutes on the ice as 50 μl 1 mM EDTA/PBS suspension. Free antibody was removed by conducting washing twice with 1 ml of 1 mM EDTA/PBS, and the cells were resuspended in 1 ml of 1 mM EDTA/PBS. Using this, detection for the modification factor on the cell surface was conducted by BD FACS Callibur (BD Bioscience).

(11) Quantitization of TGF-β1

Secretion amount of TGF-β1 in the washing solutions of the nasal cavity and the alveoli was quantitized by ELISA assay. The ELISA assay was conducted using TGF-β1 ELISA kit (BIOSOURCE INTERNATIONAL, California, USA) according to the instruction attached to the kit.

(12) Quantitization of Various Cytokines

The amounts of cytokines secreted, respectively in the washing solutions of the nasal cavity and the alveoli and from the lymphocytes of the spleen (Interleukin 4: IL-4, IL-5, IL-6 and IL-13), were quantitized by marketed ELISA kit.

(13) Preparation of PSF-3 Comprising Synthetic Peptides of SP-B and SP-C and Phospholipid Each peptide of SP-B 253-278 (SEQ ID No. 16) and SP-C 24-58 (SEQ ID No. 21) was chemically synthesized by known method. These peptides were added to a phospholipid membrane (dipalmitoyl phosphatidyl choline (75), phosphatidylglycerol (25) and palmitic acid (10)) to prepare a phospholipid membrane of plate form, and AD vehicle PSF-3 was prepared.

Example 1

Comparison of Nasal Influenza Vaccine and Subcutaneous-Injection Influenza Vaccine on Virus Growth Inhibition Action As the nasal vaccine, 0.1 μg of the split-type influenza vaccine was administered to both noses of BALB/c mouse by 1 μl, respectively as a PBS solution, alone or with 0.1 μg of 1-butanol-extracted (excluding SP-A and SP-D) surfactant (PSF-2 below) as the "AD vehicle", or 0.1 μg of CTB. As the subcutaneous-injection vaccine, the vaccine in the same amount as that of the nasal vaccine was administered as 50 μl PBS solution in total to the hypoderma of the neck of BALB/c mouse, alone or with adding PSF-2 as the AD vehicle or CTB as an adjuvant. After 4 weeks, second immunization was conducted in the same manner as in the first immunization. To the control group, same amount of PBS was administered, respectively. 2 weeks after the second immunization, influenza virus of $6.6\times10^4$ PFU was subjected to nasal infection as 3 μl PBS solution. 3 days after the infection, the mouse was slaughtered, and the washing solutions of the nasal cavity and the alveoli were prepared, and using this, evaluation of virus infection value was conducted (n=15-20; average±SE; *, the significance level by T-test was $p<0.01$ to the vaccine administration group)

As shown in FIGS. 1 (*a*) and (*b*), in case of nasal influenza vaccine administration, growth of the influenza virus in the washing solutions of the nasal cavity and the alveoli was inhibited even by the independent vaccine administration, but PSF-2 or CTB reinforced the effects significantly and growth of the influenza was nearly perfectly inhibited, ensuring the effects of the vaccine. Though now shown in the figure, in the case of using PSF-1 or PSF-3 instead of PSF-2, similar effects were obtained. Similar phenomena were also found for PSF-4 and -5, but the effects were attenuated.

Though now shown in the figure, even in case that PSF-2 or CTB were nasally administered as independent, respectively in the first immunization and the second immunization, inhibitory effects for virus growth were not found in either case, and thus the effects of PSF-2 or CTB were determined as reinforcement effects for the vaccine effects.

On the other hand, in case of subcutaneous-injection influenza vaccine, as shown in (*c*) and (*d*) of FIG. 1, the titer (PFU) of the influenza virus in the washing solutions of the nasal cavity and the alveoli was reduced significantly even with the independent vaccine, so the effects of the vaccine was found, but reinforcement effects of PSF-2 or CTB were not found. In other words, in case of subcutaneous administration, nearly no or very little reinforcement effects of PSF-2 or CTB on immunity were found. Though now shown in the figure in this experiment, even in case that PSF-2 or CTB is subcutaneously administered as independent, respectively in the first immunization and the second immunization, inhibitory effects for virus growth were not found in either case. Though now shown in the figure, in the case of using PSF-1, PSF-3, PSF-4 and PSF-5 instead of PSF-2, reinforcement effects on the vaccine action were not found.

Example 2

Influence of PSF-2 or CTB on Production of Anti-Influenza Specific Antibodies (IgA and IgG) in the Washing Solution of the Nasal Cavity After (a) nasal and (b) Subcutaneous-Injection Influenza Vaccine Administration In the same manner as described in FIG. 1, as the nasal vaccine, 0.1 μg of the split-type influenza vaccine was administered to both noses of BALB/c mouse by 1 μl, respectively, i.e., 2 μl in total as a PBS solution, alone or with 0.1 μg of PSF-2 as the "AD vehicle", or 0.1 μg of CTB as an adjuvant. As the subcutaneous vaccine, the vaccine in the same amount as that of the nasal vaccine, PSF-2 or CTB was administered as 50 μl PBS solution to the hypoderma of the neck of BALB/c mouse. After 4 weeks, second immunization was conducted in the same manner as in the first immunization. To the control group, same amount of PBS was administered, respectively. 2 weeks after the second immunization, influenza virus of $6.6\times10^4$ PFU was subjected to nasal infection as 3 μl PBS solution. 3 days after the infection, the mouse was slaughtered, and the washing solution of the nasal cavity was prepared, and using this, evaluation of virus infection value was conducted (n=15-20; average±SE; *, the significance level by T-test was $p<0.01$ to the vaccine administration group).

Figure 2:
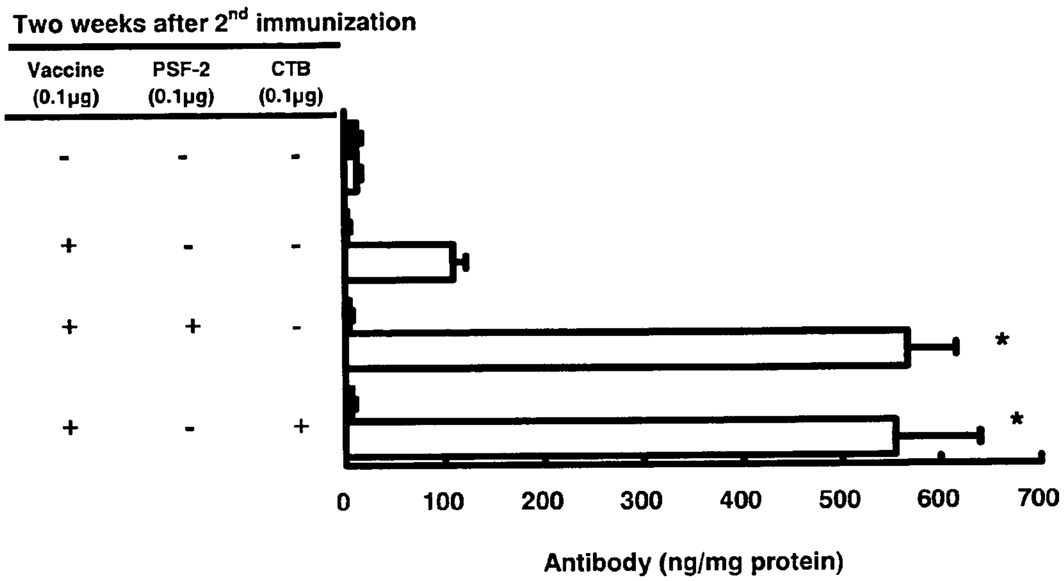
FIG. 2 represents the amounts of IgA and IgG, which produces anti-influenza antibody in the nasal cavity-washing solution by influenza vaccine of (a) nasal administration and (b) subcutaneous injection. The white bar represents IgA amount, and the black bar represents IgG amount, respectively. (Example 2)
Figure 2:
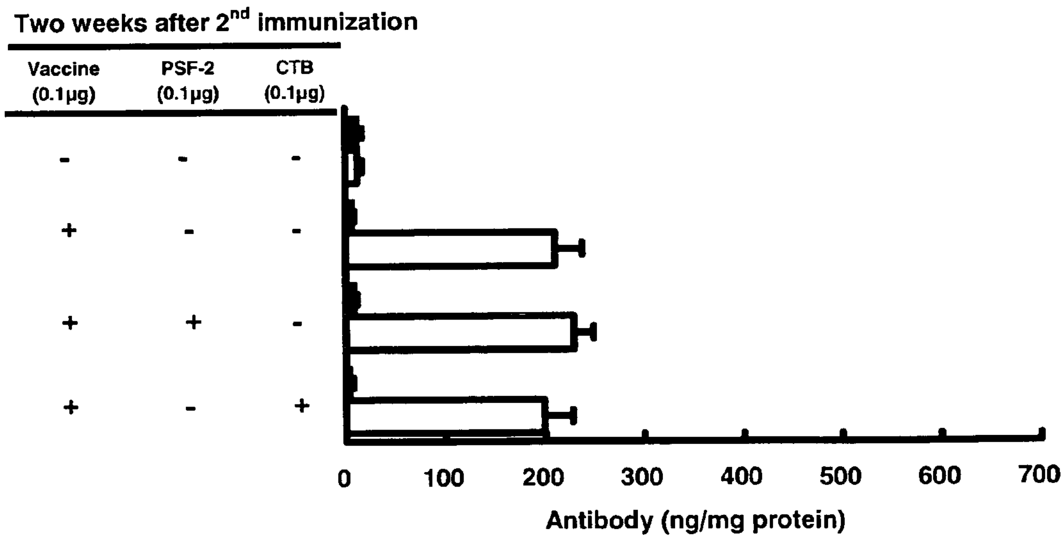

The results are shown in FIGS. 2 (*a*) and (*b*). By the split-type influenza vaccine nasally administered, anti-influenza specific IgA was selectively produced in the nasal cavity, and thus increased in the washing solution, but PSF-2 or CTB increased the amount of this specific IgA in equivalent extent remarkably. On the other hand, even in case of the subcutaneous injection, increase of specific IgA amount in the washing solution of the nasal cavity by independent split-type influenza vaccine was found, but the extent was low compared to that of the nasal administration. In addition, in case of the subcutaneous injection of the vaccine, immunity reinforcement effects of PSF-2 or CTB were not found in either case in production of IgA or IgG. Though now shown in the figure, in the case of using PSF-1 or PSF-3 instead of PSF-2, similar effects were obtained. Similar phenomena were also found for PSF-4 and -5, but the effects were attenuated.

Example 3

Influence of PSF-2 or CTB on Production of Anti-Influenza Specific Antibodies (IgA and IgG) in the Washing Solution of the Lung by Influenza Vaccine of (a) Nasal Administration and (b) Subcutaneous-Injection As the nasal vaccine, 0.1 μg of the split-type influenza vaccine was administered to both noses of BALB/c mouse by 1 μl, respectively, i.e., 2 μl in total as a PBS solution, alone or with 0.1 μg of PSF-2 as the "AD vehicle", or 0.1 μg of CTB as an adjuvant. As the subcutaneous vaccine, the vaccine in the same amount as that of the nasal vaccine, PSF-2 or CTB was administered as 50 μl PBS solution to the hypoderma of the neck of BALB/c mouse. After 4 weeks, second immunization was conducted in the same manner as in the first immunization. To the control group, same amount of PBS was administered, respectively. 2 weeks after the second immunization, influenza virus of $6.6\times10^4$ PFU was subjected to nasal infection as 3 μl PBS solution. 3 days after the infection, the mouse was slaughtered, and the washing solution of the lung was prepared, and using this, influence of the antigen-drug vehicle on production of anti-influenza specific antibodies (IgA and IgG) was investigated (n=15-20; average±SE; *, the significance level by T-test was p<0.01 to the vaccine administration group).

Figure 3:
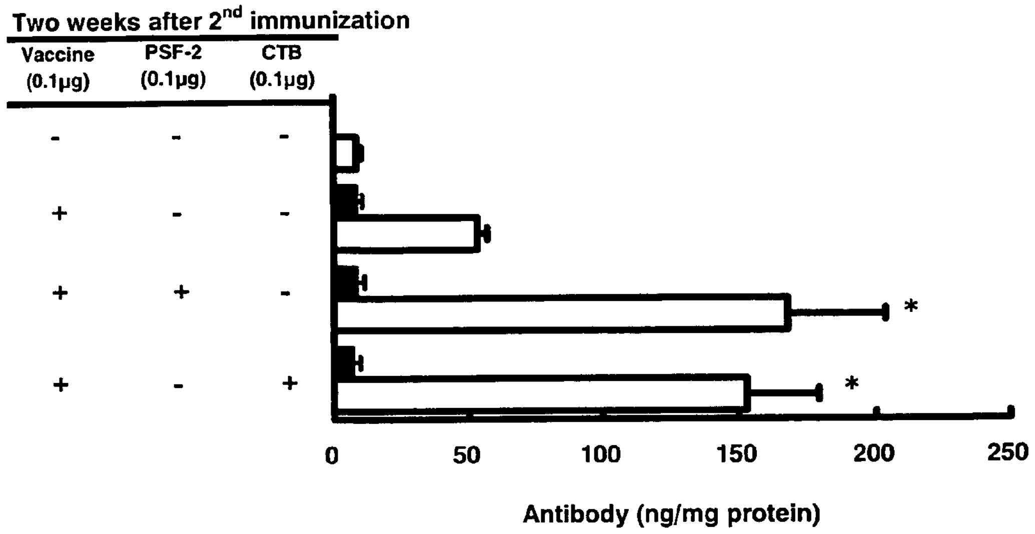
FIG. 3 represents the influence of the adjuvant on production of anti-influenza specific antibodies, IgA and IgG in the lung-washing solution by influenza vaccine of (a) nasal administration and (b) subcutaneous injection. (Example 3)
Figure 3:
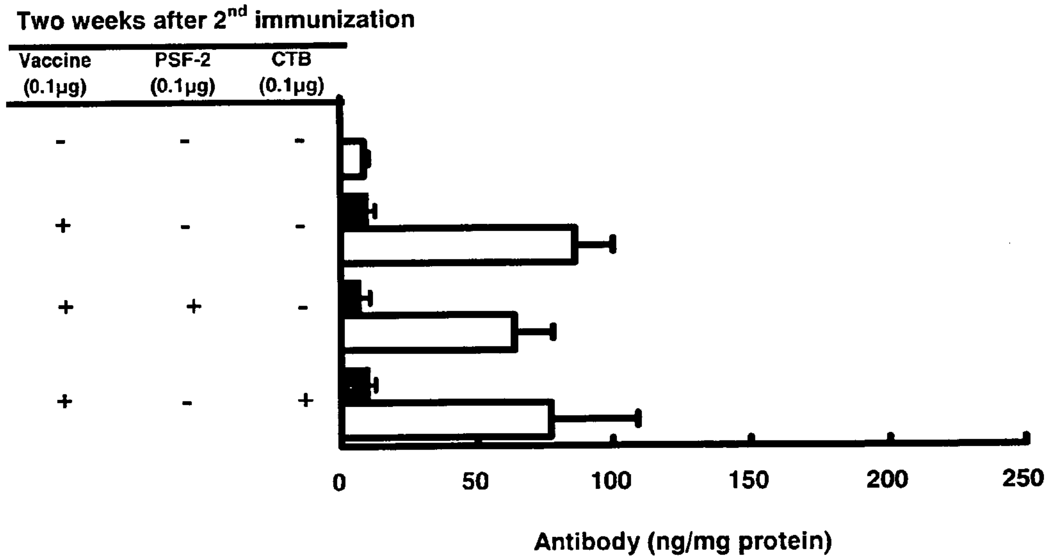

As shown in FIGS. 3 (*a*) and (*b*), promoting effects of PSF-2 or CTB on production of anti-influenza specific antibodies were remarkable, similarly to the case of nasal administration of the vaccine, and there was no big difference between them. This immunity reinforcement effects were specific for IgA, and not found for IgG. In case of the subcutaneous injection, increase of IgA in the washing solution of the lung, but immunity reinforcement effects of PSF-2 or CTB were not found similarly to the case of the washing solution of the nasal cavity. Though now shown in the figure in this experiment, even in case that PSF-2 or CTB was administered nasally or subcutaneously as independent, respectively in the first immunization and the second immunization, increase of virus-specific IgA or IgG in the washing solution of the lung was not found in either case, and thus the effects of PSF-2 or CTB were determined as reinforcement effects for the vaccine actions. Though now shown in the figure, in the case of using PSF-1 or PSF-3 instead of PSF-2, similar effects were obtained. Similar phenomena were also found for PSF-4 and -5, but the effects were attenuated.

Example 4

Influence of PSF-2 or CTB on Production of Anti-Influenza Specific Antibodies (IgA and IgG) in the Blood by Influenza Vaccine of (a) Nasal Administration and (b) Subcutaneous-Injection As the nasal vaccine, 0.1 μg of the split-type influenza vaccine was administered to both noses of BALB/c mouse by 1 μl, respectively, i.e., 2 μl in total as a PBS solution, alone or with 0.1 μg of PSF-2 as the "AD vehicle", or 0.1 μg of CTB as an adjuvant. As the subcutaneous vaccine, the vaccine in the same amount as that of the nasal vaccine, PSF-2 or CTB was administered as 50 μl PBS solution to the hypoderma of the neck of BALB/c mouse. After 4 weeks, second immunization was conducted in the same manner as in the first immunization. To the control group, same amount of PBS was administered, respectively. 2 weeks after the second immunization, the mouse was slaughtered, blood collection from the heart was conducted, and the serum was prepared from this, and quantitization of the expression amount of anti-influenza antibodies was conducted using this (n=15-20; average±SE).

Figure 4:
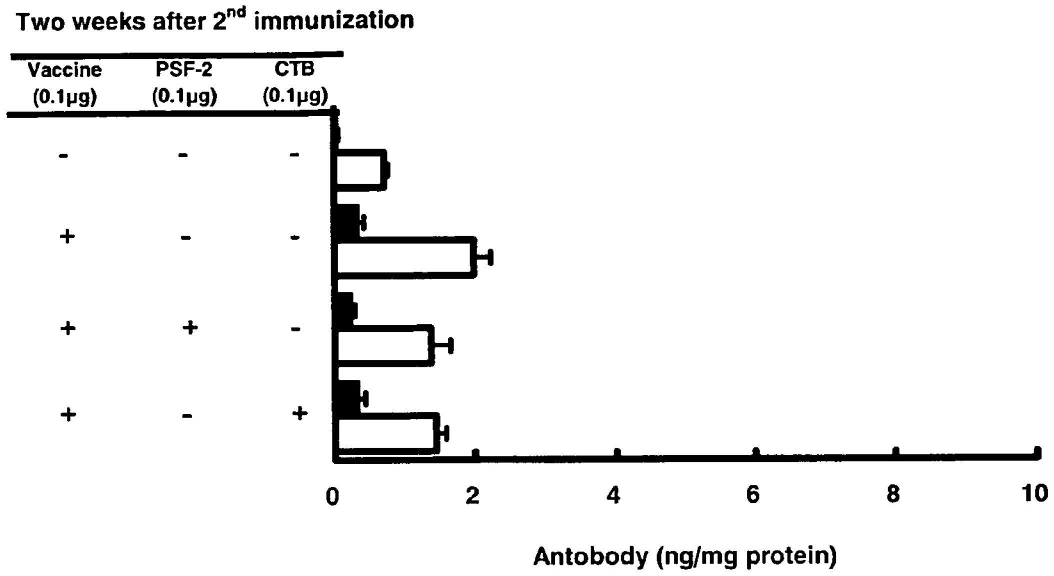
FIG. 4 represents the influence of PSF-2 and CTB on production of blood anti-influenza specific antibodies, IgA and IgG by influenza vaccine of (a) nasal administration and (b) subcutaneous injection. (Example 4)
Figure 4:
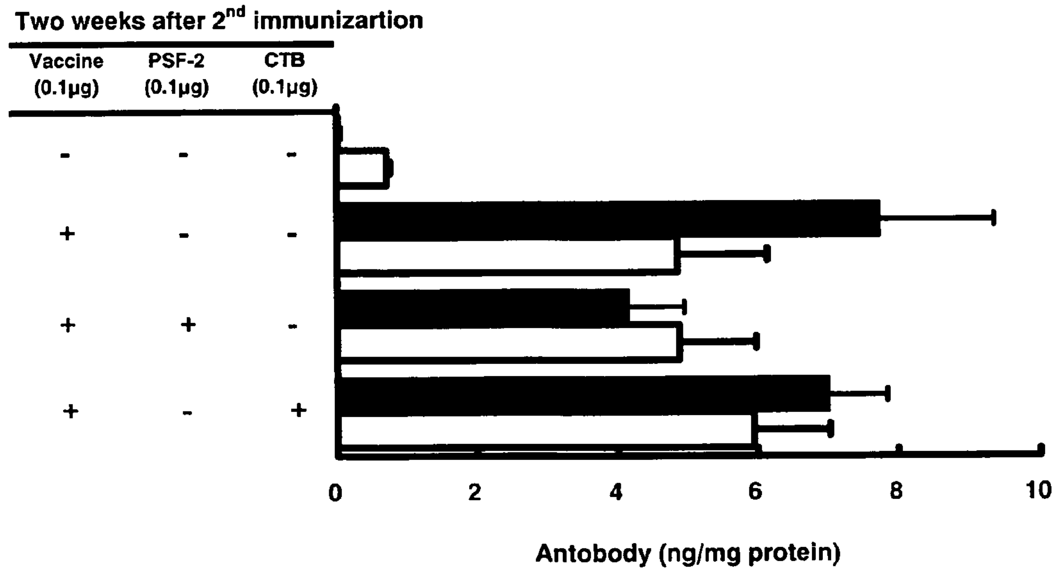

As shown in FIGS. 4 (*a*) and (*b*), for the production amount of blood anti-influenza antibodies IgA (white bar) and IgG (black bar), slight increase of IgA or IgG was found in nasal vaccine administration, but increase of IgA or IgG by PSF-2 or CTB was not found, and thus iummunity reinforcement effects were not found. On the other hand, in case of the subcutaneous injection, remarkable increase of IgG and definite increase of IgA were found by the split-type influenza vaccine, but also in this case, increase of antibody production by PSF-2 or CTB was not found and thus immunity reinforcement effects were not found. Particularly, in case of the subcutaneous injection, IgG increased specifically in blood. In the case of using PSF-1 instead of PSF-2, nearly similar effects were obtained (not shown in the figure).

In addition, even in case that PSF-2 or CTB was administered nasally or subcutaneously as independent, respectively in the first immunization and the second immunization, increase of virus-specific IgA or IgG in blood was not found, and thus the effects of PSF-2 or CTB were determined as reinforcement effects for the vaccine actions (not shown in the figure).

Example 5

Influence of PSF-2 or CTB on Antigen-Presenting Ability of Dendritic Cells of the Nose, Lung or Spleen by Influenza Vaccine of (a) Nasal Administration and (b) Subcutaneous-Injection As the nasal vaccine, 0.1 μg of the split-type influenza vaccine was administered to both noses of BALB/c mouse in 2 μl in total as 1 μl PBS solution, alone or with 0.1 μg of PSF-2, or 0.1 μg of CTB. As the subcutaneous vaccine, the split-type influenza vaccine in the same amount as that of the nasal vaccine, PSF-2 or CTB was administered as 50 μl PBS solution to the hypoderma of the neck of BALB/c mouse. After 2 days, the mouse was slaughtered, and the dendritic cells were prepared from the nose, lung or spleen, and expression level of MHC class II, CD40, B7-1 (CD80) and B7-2 (CD80) on the cell surface was measured by flow cytometry.

As a result, increase of expression of antigen-presenting related molecules, CD40 and B7-2 was found on the membrane surface of the dendritic cells (antigen-presenting cells) in the nose, where the vaccine had been challenged by CTB, and adjuvants effects were found in molecular level. In case of PSF-2, increase of expression of MHC II molecule was also found in addition to CD40 and B7-2 of the dendritic cells in the nose, and it was shown that at least three molecules of the dendritic cells are involved in the immunity reinforcement effects.

However, definite change was not found in CD40, B7-2 or MHC II molecule of the dendritic cells in the lung and spleen. In the case of using PSF-1 or PSF-3 instead of PSF-2, nearly similar effects were obtained. Similar phenomena were also found for PSF-4 and -5, but the effects were attenuated.

Example 6

Influence of SPF-2 or CTB on TGF-β1 Secretion Level in the Mucosal Membrane of (a) the Nasal Cavity and (b) the Alveoli by Nasal Administration of Influenza Vaccine As the nasal vaccine, 0.1 μg of the split-type influenza vaccine was administered to both noses of BALB/c mouse in 2 μl in total as 1 μl PBS solution, alone or with 0.1 μg of SPF-2, or 0.1 μg of CTB. As the subcutaneous vaccine, the vaccine in the same amount as that of the nasal vaccine, PSF-2 or CTB was administered as 50 μl PBS solution to the hypoderma of the neck of BALB/c mouse. After 4 weeks, second immunization was conducted in the same manner as in the first immunization. To the control group, same amount of PBS was administered, respectively. 2 weeks after the second immunization, the mouse was slaughtered, and the washing solution of the nasal cavity was prepared, and using this, quantitization of TGF-β1 secretion amount was conducted (n=15-20; average±SE; *, the significance level by T-test was p<0.01 to the vaccine administration group).

It has been known that for differentiation of B cell to IgA-production cell (class switch), local TGF-β1 concentration present in the production cell is important (Stavnezer, J.: Regulation of antibody production and class switching by TGF-beta. J. Immunol. 155(4), 1647-1651, 1995). Herein, TGF-β1 concentration in a local mucosal membrane of (a) the nasal cavity or (b) the alveoli was investigated.

Figure 5:
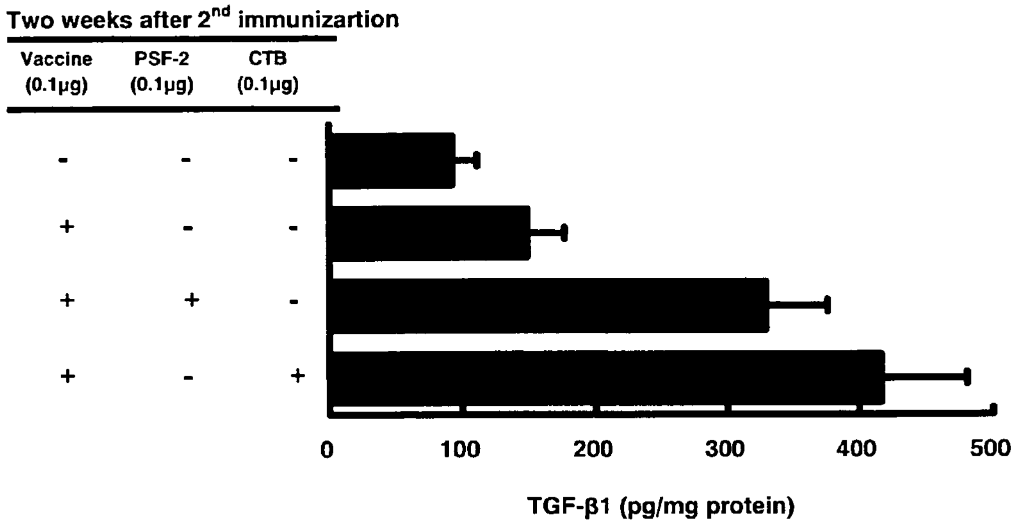
FIG. 5 represents the influence of PSF-2 and CTB on the secretion level of TGF-β1 in the mucosal membranes of (a) the nasal cavity and (b) the alveoli by nasal administration of influenza vaccine. (Example 6)
Figure 5:
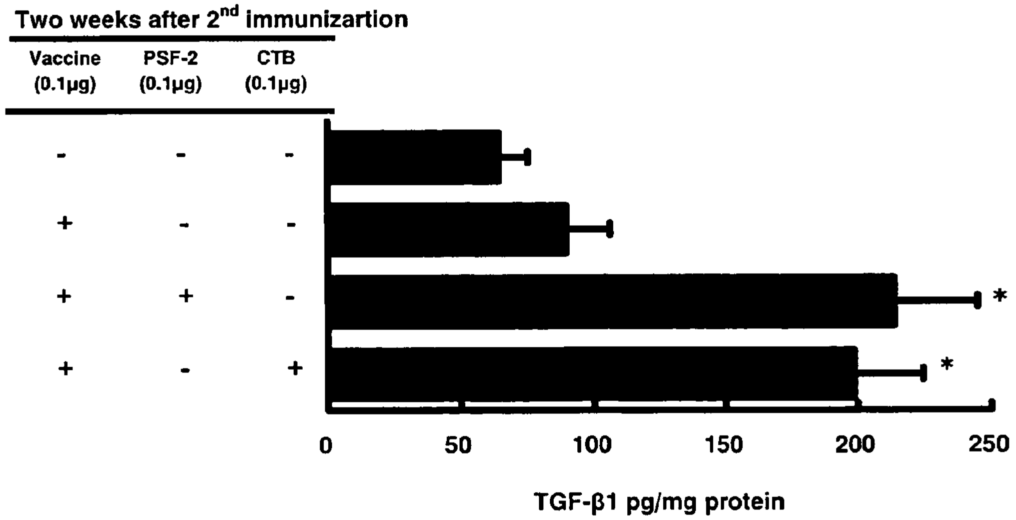

The TGF-β1 concentration in the local mucosal membrane of the nasal cavity or the alveoli where the split-type influenza vaccine was administered, increased significantly in presence of SPF-2 or CTB. The extent of increase was such that there was no significant difference between SPF-2 and CTB. The results are shown in FIGS. 5(*a*) and (*b*). It was found that SPF-2, which was derived from the living body, increased TGF-β1 concentration which urges promotion of differentiation of B cell secreting IgA as much as CTB, which is exogenous toxin. Though not shown in the figure, in the case of using PSF-1 or PSF-3 instead of PSF-2, nearly similar effects were obtained. Similar phenomena were also found for PSF-4 and -5, but the effects were attenuated. In addition, even in case that PSF-2 or CTB was administered nasally or subcutaneously as independent, respectively in the first immunization and the second immunization, increase of TGF-β1 concentration was not found, and thus the effects of PSF-2 or CTB were determined as reinforcement effects for the vaccine actions (not shown in the figure).

Example 7

Influence of PSF-2 or CTB on Production of Anti-Influenza Specific Antibodies (IgA and IgG) in (a) the Nasal Cavity, (b) the Alveoli and (c) the Blood by Nasal Administration of Influenza Vaccine As the nasal vaccine, 0.2 μg of the split-type influenza vaccine was administered to both noses of BALB/c mouse by 1 μl, respectively, i.e., 2 μl in total as a PBS solution, alone or with 0.2 μg of PSF-2 as the "AD vehicle", or 0.2 μg of CTB as an adjuvant. After 4 weeks, second immunization was conducted in the same manner as in the first immunization. To the control group, same amount of PBS was administered, respectively. 2 weeks after the second immunization, the mouse was slaughtered in each group, and the washing solutions of the nasal cavity and the alveoli, and serum by blood collection from the heart were prepared, and using these, quantitization of expression amount of anti-influenza antibody was conducted (n=15-30; average±SE; +, $p<0.01$ vs. the vaccine independent administration).

Figure 6:
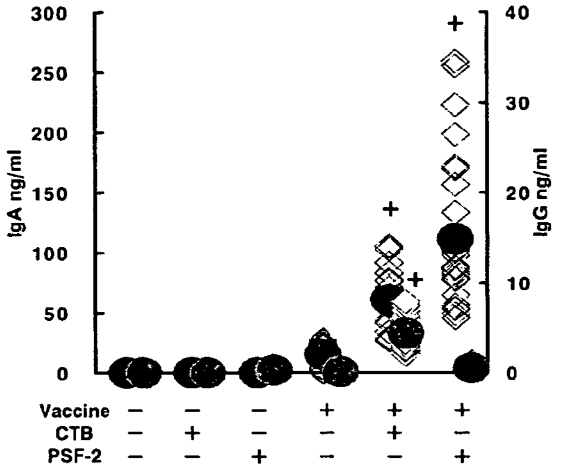
FIG. 6 represents the influence of PSF-2 and CTB on production of anti-influenza specific antibody in (a) the nasal cavity, (b) the alveoli and (c) the blood by nasal administration of influenza vaccine. (Example 7)
Figure 6:
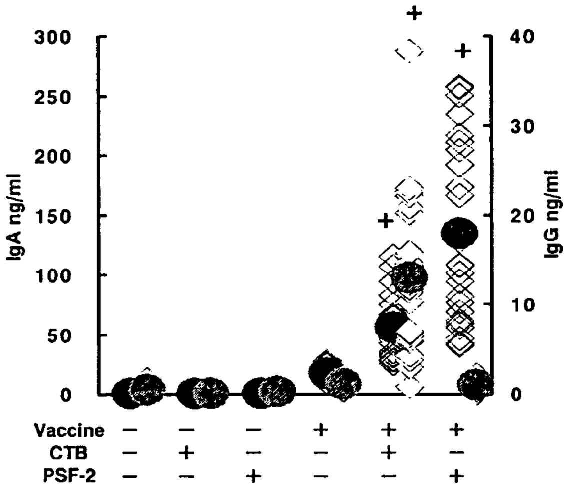
Figure 6:
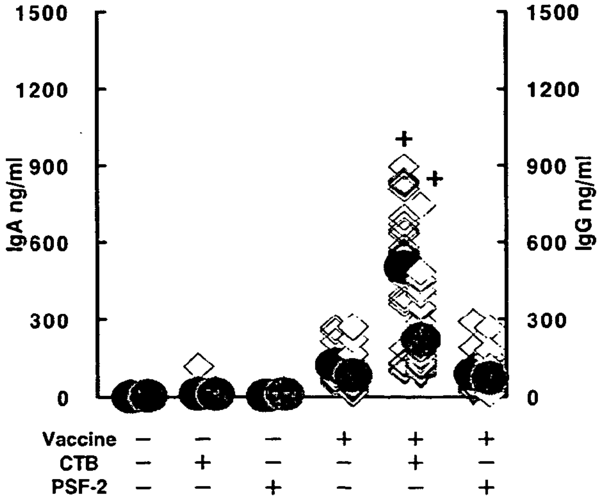

As shown in FIGS. 6 (*a*) and (*b*), in the washing solutions of the nasal cavity and the alveoli, blood anti-influenza antibody IgA (blue circlet) showed remarkable increase in case that PSF-2 and the vaccine were administered. However, as shown in FIG. 6 (*c*), increase of IgG (red circlet) in blood was not found.

On the other hand, in case that CTB and the vaccine were administered, IgG and IgG increased in the washing solutions of the nasal cavity and the alveoli (FIGS. 6 (*a*) and (*b*)), and also remarkably in blood (FIG. 6 (*c*)).

As described above, in case of CTB, it reacted with the antigen inoculated nasally, and caused systemic immune response, as well as establishment of local immunity, as reported conventionally. On the other hand, in case of PSF-2, it only established local mucosal immunity.

In addition, J. Freek van Iwaarden, et al. (Non-Patent Document 4) have reported that if macrophage is removed artificially from the lung, SP-B and lipid can induce systemic immune reaction, but in the case that macrophage is not removed, they cannot induce immunity. In addition, in this document, the amount of SP-B plus lipid necessary for induction of the systemic immune reaction, is 250 to 300 μl, which is quite different from the PSF-2 administration amount in the above-mentioned Examples (0.2 μl). However, it has never mentioned local mucosal immunity.

Example 8

Influence of SPF-2 or CTB on Various Cytokines Secreted From the Nose, Lung or Lymphocyte of Spleen by Nasal Administration of Influenza Vaccine As the nasal vaccine, 0.2 μg of the split-type influenza vaccine was administered to the upper respiratory tract of BALB/c mouse in 2 μl in total as 1 μl PBS solution, alone or with 0.2 μg of PSF-2 or 0.2 μg of CTB. 2 weeks after the second immunization, the mouse was slaughtered, and quantitization of secretion amount of TGF-β1 and cytokines (IL-4, IL-5, IL-6 and IL-13) from the nose, lung or lymphocyte of spleen was conducted (n=15-20; average±SE; +++, p=0.06; ++, P=0.05; +, P=0.01 vs. the vaccine independent administration).

Figure 7:
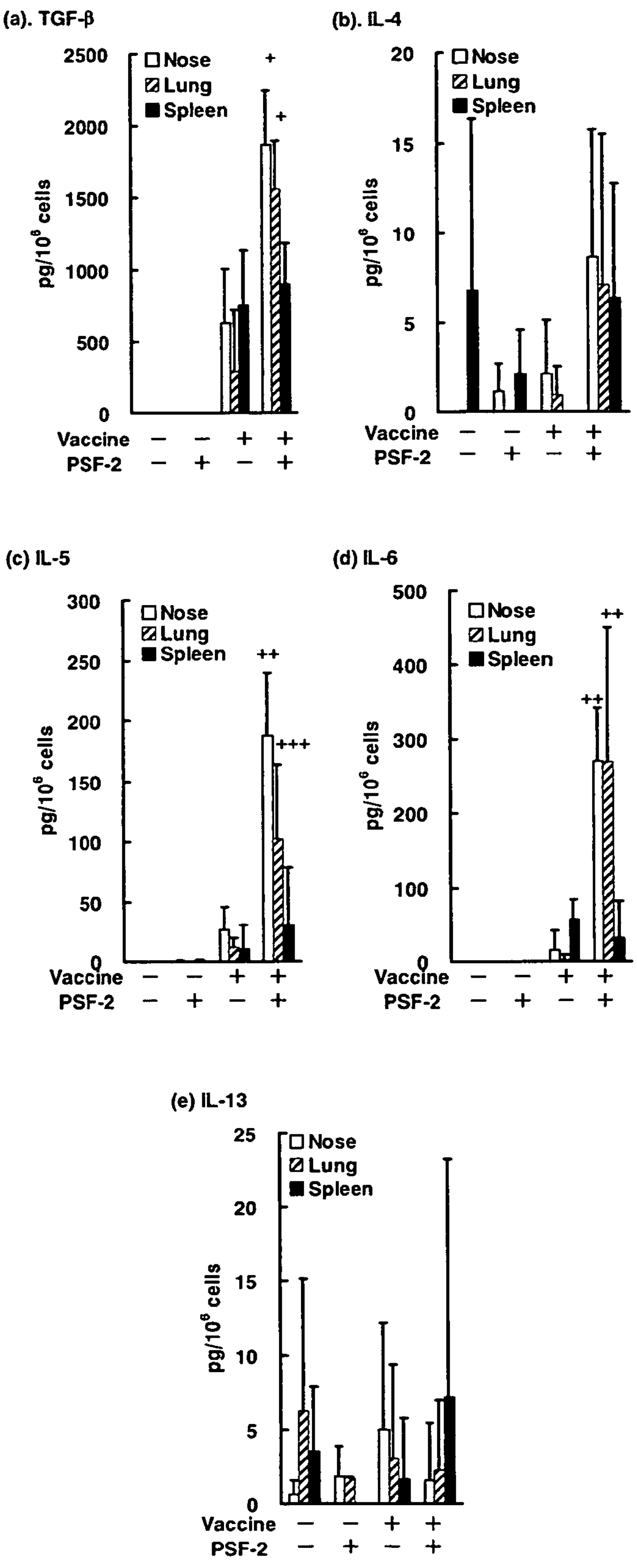
FIG. 7 represents the influence of SPF-2 and CTB on production of various cytokines which is secreted from the nasal cavity, the alveoli and lymphocyte of the spleen by nasal administration of influenza vaccine. (Example 8)

As shown in FIGS. 7 (*a*) to (*e*), TGF-β1, IL-5 and IL-6 were found to increase significantly in secretion, whereas IL-4 and IL-13 were found to increase significantly in the local mucosal membrane (nose, lung) after the vaccine immunity along with PSF-2. On the other hand, significant increase of any cytokine was not observed in the spleen.

From the above results, it was found that PSF-2 increase Th2-type cytokine, which promotes differentiation and induction of B cell producing IgA.

Example 9

Influence of PSF-3 on Production of Anti-Influenza Specific Antibodies (IgA and IgG) in (a) the Nasal Cavity, (b) the Alveoli and (c) the Blood by Nasal Administration of Influenza Vaccine As the nasal vaccine, 0.2 μg of the split-type influenza vaccine was administered to both noses of BALB/c mouse by 1 μl, respectively, i.e., 2 μl in total as a PBS solution, alone or with 0.2 μg of PSF-3 (a mixture of same amount of SP-B fragment, i.e., 253 to 278 peptides described in SEQ ID No. 16, and SP-C fragment, i.e., 24 to 58 peptides described in SEQ ID No. 21) as the "AD vehicle", or 0.2 μg of lipid ingredient. After 4 weeks, second immunization was conducted in the same manner as in the first immunization. To the control group, same amount of PBS was administered, respectively. 2 weeks after the second immunization, the mouse was slaughtered in each group, and the washing solutions of the nasal cavity and the alveoli, and serum by blood collection from the heart were prepared, and using these, quantitization of expression amount of anti-influenza antibody was conducted (n=15-30; average±SE; +, $p<0.01$ vs. the vaccine independent administration).

Figure 8:
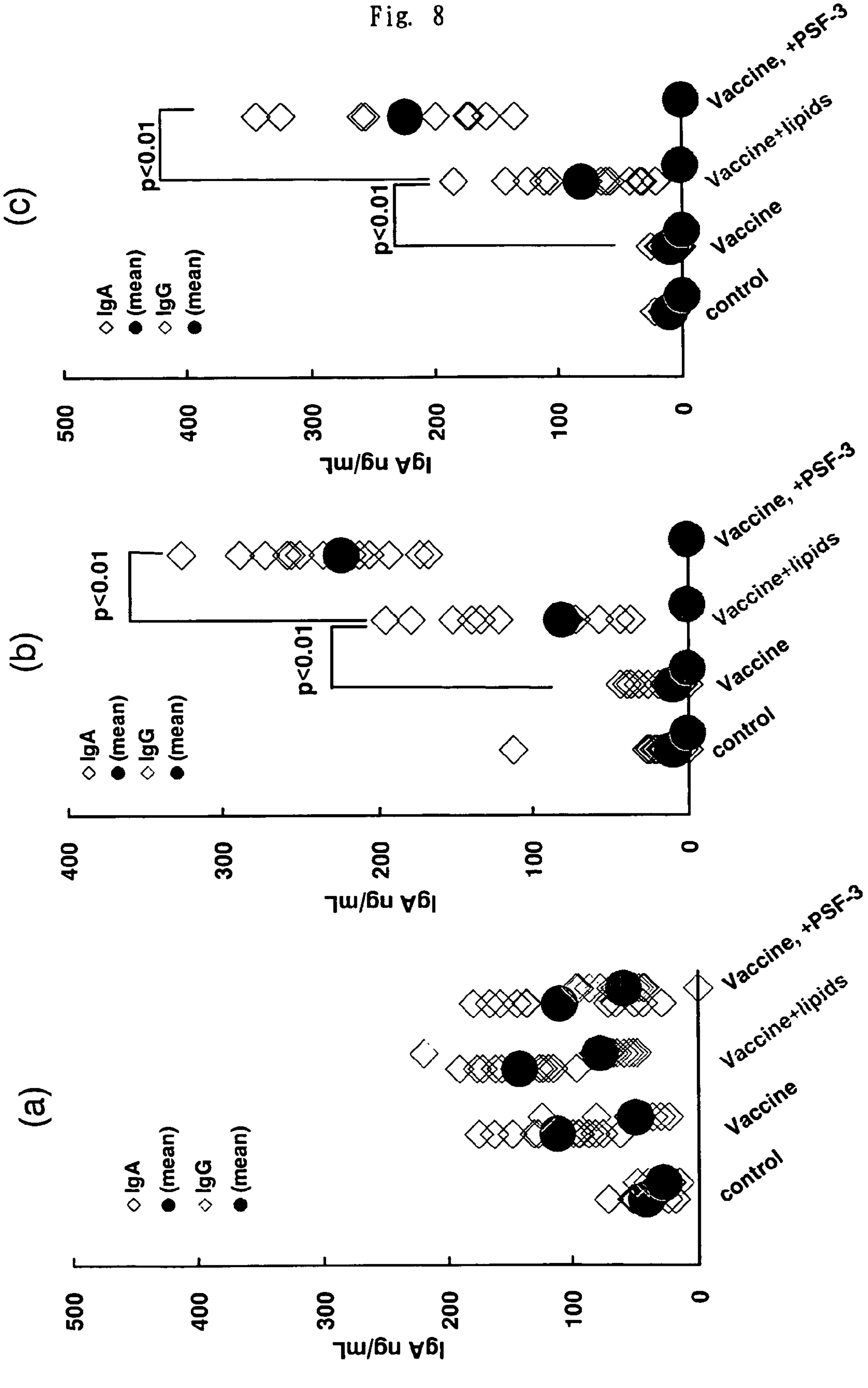
FIG. 8 represents the influence of PSF-3 on production of anti-influenza specific antibody in (a) the nasal cavity, (b) the alveoli and (c) the blood by nasal administration of influenza vaccine. (Example 9)

As shown in FIGS. 8 (*a*) and (*b*), in the washing solutions of the nasal cavity and the alveoli, blood anti-influenza antibody IgA (blue circlet) showed remarkable increase in case that PSF-3 and the vaccine were administered, but significant increase of IgG (red circlet) was not found. On the other hand, in serum (*c*), neither IgA (blue circlet) nor IgG (red circlet) was found to increase significantly.

INDUSTRIAL APPLICABILITY

The "AD vehicle" according to the present invention, exerts a function of transporting all the substances such as antigen, drug, nutrient, and the like from the mucosal membrane of the nose, trachea, intestine, and the like, or the skin into cells, and also induces preferential and selective production of IgA, enabling a mucosal vaccine, prevention and treatment of allergy, transmucosal and transdermal DDS, and transmucosal and transdermal administration of useful substance such as a drug, nutrient, and the like. Furthermore, it has been approved already for its clinical use and safety in this country or other countries.

Accordingly, application and use of the "AD vehicle" is expected in very broad range of industries such as medication/pharmaceutics in biological preparations, DDS, and the like, food and drink industries in functional food, health food, and the like, agriculture and agricultural chemicals in raising and cultivation of agricultural products, anti-disease measures, insect destruction, and the like, cultivation fishery in fish-disease vaccine and administration thereof, and the like, architecture or environment preservation in anti-ant, anti-insect, and the like.

The invention claimed is:

1. A composition for inducing mucosal immunity against an influenza virus by promoting the production of an IgA antibody against the virus in a local mucosal membrane, comprising an influenza virus split antigen and an antigen-drug vehicle which is a complex consisting of:

a pulmonary surfactant protein B or a peptide consisting of the amino acid sequence of SEQ ID NO: 2, 7, 8, 10, 11, 12, 13, 14, 15, 16, 17, 18, 19 or 20, a pulmonary surfactant protein C or a peptide consisting of the amino acid sequence of SEQ ID NO: 4, 9, 21 or 6, and at least one lipid selected from the group consisting of phosphatidyl choline, dipalmitoyl phosphatidyl choline, phosphatidyl serine, dipalmitoyl glycerophosphocholine, diacyl glycerophosphoglycerol, phosphatidylglycerol, phosphatidyl inositol, phosphatidyl ethanolamine, phosphatidic acid, lauric acid, myristic acid, palmitic acid, stearic acid and oleic acid, wherein the composition is suitable for nasal administration.

2. The composition according to claim 1, wherein the induction of mucosal immunity is further made by promoting the production of TGF-β1 and Th2 type cytokine against the influenza virus in the local mucosal membrane.

3. A method of inducing mucosal immunity, which comprises administering the composition according to claim 1, into a nasal cavity or upper respiratory tract of a subject in need thereof.

4. The method of inducing mucosal immunity according to claim 3, wherein the induction of mucosal immunity is made by promoting the production of an IgA antibody in the local mucosal membrane.

5. The method of inducing mucosal immunity according to claim 3, wherein the induction of mucosal immunity is made by promoting the production of TGF-β1 and Th2 type cytokine in the local mucosal membrane.

* * * * *